(12) United States Patent
Freudenthal

(10) Patent No.: US 10,631,839 B2
(45) Date of Patent: Apr. 28, 2020

(54) IMPLANTABLE DEVICE

(75) Inventor: Franz Freudenthal, La Paz (BO)

(73) Assignee: PFM MEDICAL AG, Cologne (DE)

( * ) Notice: Subject to any disclaimer, the term of this patent is extended or adjusted under 35 U.S.C. 154(b) by 1294 days.

(21) Appl. No.: 10/543,007

(22) PCT Filed: Jan. 21, 2004

(86) PCT No.: PCT/EP2004/000451
§ 371 (c)(1),
(2), (4) Date: May 2, 2006

(87) PCT Pub. No.: WO2004/064671
PCT Pub. Date: Aug. 5, 2004

(65) Prior Publication Data
US 2006/0224183 A1    Oct. 5, 2006

(30) Foreign Application Priority Data
Jan. 21, 2003 (DE) .................................. 103 02 447

(51) Int. Cl.
*A61B 17/12* (2006.01)
*A61B 17/221* (2006.01)
(Continued)

(52) U.S. Cl.
CPC .... *A61B 17/0057* (2013.01); *A61B 17/12027* (2013.01); *A61B 17/12031* (2013.01);
(Continued)

(58) Field of Classification Search
CPC .......... A61B 90/39; A61B 2017/00592; A61B 2017/00606; A61B 17/12022;
(Continued)

(56) References Cited

U.S. PATENT DOCUMENTS

| 4,856,516 A | 8/1989 | Hillstead |
| 4,994,069 A | 2/1991 | Ritchart et al. |

(Continued)

FOREIGN PATENT DOCUMENTS

| DE | 2822603 | 11/1979 |
| DE | 158084 | 12/1982 |

(Continued)

OTHER PUBLICATIONS

Transmittal of Translation of International Preliminary Report on Patentability received in corresponding PCT Application (9 pages).

(Continued)

*Primary Examiner* — Jing Rui Ou
(74) *Attorney, Agent, or Firm* — Grossman, Tucker, Perreault & Pfleger, PLLC

(57) ABSTRACT

Disclosed is an implantable device (1) to be used in a human and/or animal body for occluding or partially occluding defective openings, hollow spaces, organ tracts, etc. or creating a defined connecting opening between walls, organs, hollow spaces, etc. Said implantable device (1) comprises a support structure which has a great length-to-width ratio along an axis (63) in a first operating state (primary shape) while having a smaller length-to-width ratio along said axis (63) in a second operating state (secondary shape). The support structure is provided with a proximal (20) and a distal section (30) and is formed from a single wire-type element (10) by intercoiling and/or intertwining and/or interweaving like a tissue and/or a cluster and/or a net. Also disclosed is a placing system especially for such an implantable device, comprising an advancing element (5), a directing wire (6,9) and/or an inner mandrin, and at least one holding wire (80,81). The directing wire (6) and the at least one holding wire (80,81) are used for cooperating with a proximal end of the implantable device (1), the implantable (Continued)

Figure 1:
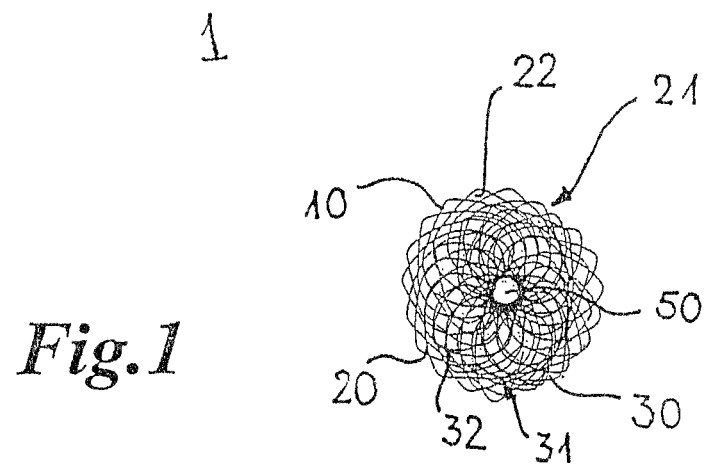

device (1) being transformable from a primary shape into a secondary shape and vice versa by moving the holding wire (80, 81) and the directing wire (6) relative to the advancing element (5).

22 Claims, 18 Drawing Sheets

(51) Int. Cl.
*A61B 17/00* (2006.01)
*A61F 2/88* (2006.01)
*A61F 2/01* (2006.01)
*A61F 2/30* (2006.01)
*A61B 90/00* (2016.01)

(52) U.S. Cl.
CPC .. *A61B 17/12036* (2013.01); *A61B 17/12109* (2013.01); *A61B 17/12172* (2013.01); *A61B 17/12177* (2013.01); *A61B 17/221* (2013.01); *A61B 17/12022* (2013.01); *A61B 90/39* (2016.02); *A61B 2017/00575* (2013.01); *A61B 2017/00592* (2013.01); *A61B 2017/00597* (2013.01); *A61B 2017/00606* (2013.01); *A61B 2017/00867* (2013.01); *A61F 2/01* (2013.01); *A61F 2/88* (2013.01); *A61F 2002/30093* (2013.01); *A61F 2210/0019* (2013.01)

(58) Field of Classification Search
CPC .......... A61B 17/0057; A61B 17/12031; A61B 17/12109; A61B 17/12177; A61B 17/12027; A61B 17/12036; A61B 17/12172; A61B 17/221; A61B 2017/00575; A61B 2017/00597; A61B 2017/00867; A61F 2/88; A61F 2210/0019; A61F 2/01; A61F 2002/30093
USPC .................. 606/213, 232; 600/200
See application file for complete search history.

(56) References Cited

U.S. PATENT DOCUMENTS

| | | | |
|---|---|---|---|
| 5,108,420 A | 4/1992 | Marks | |
| 5,171,259 A | 12/1992 | Inoue | |
| 5,433,727 A | 7/1995 | Sideris | |
| 5,536,274 A | 7/1996 | Neuss | |
| 5,683,411 A | 11/1997 | Kavteladze et al. | |
| 5,725,552 A | 3/1998 | Kotula et al. | |
| 5,733,294 A * | 3/1998 | Forber et al. | 606/151 |
| 5,846,261 A | 12/1998 | Kotula et al. | |
| 5,876,445 A | 3/1999 | Andersen et al. | 623/11 |
| 5,944,738 A * | 8/1999 | Amplatz et al. | 606/213 |
| 5,976,174 A * | 11/1999 | Ruiz | 606/213 |
| 6,077,281 A | 6/2000 | Das | |
| 6,123,715 A | 9/2000 | Amplatz | |
| 6,171,329 B1 * | 1/2001 | Shaw et al. | 606/213 |
| 6,174,322 B1 * | 1/2001 | Schneidt | 606/213 |
| 6,214,029 B1 * | 4/2001 | Thill et al. | 606/213 |
| 6,312,446 B1 * | 11/2001 | Huebsch et al. | 606/213 |
| 6,312,455 B2 | 11/2001 | Duerig et al. | |
| 6,338,736 B1 | 1/2002 | Boosfeld et al. | |
| 6,355,052 B1 | 3/2002 | Neuss et al. | |
| 6,368,339 B1 | 4/2002 | Amplatz | |
| 6,375,671 B1 | 4/2002 | Kobayashi et al. | |
| 6,468,303 B1 * | 10/2002 | Amplatz et al. | 623/1.2 |
| 6,551,344 B2 * | 4/2003 | Thill | 606/213 |
| 6,911,037 B2 * | 6/2005 | Gainor et al. | 606/213 |
| 6,953,476 B1 | 10/2005 | Shalev | |
| 6,953,746 B2 | 10/2005 | Uesawa | |
| 2001/0007946 A1 * | 7/2001 | Lenker | A61B 17/12022 606/198 |
| 2001/0041930 A1 * | 11/2001 | Globerman et al. | 623/1.16 |
| 2002/0099437 A1 * | 7/2002 | Anson | A61B 17/0057 623/1.15 |
| 2002/0169475 A1 * | 11/2002 | Gainor et al. | 606/213 |
| 2002/0193827 A1 | 12/2002 | McGuckin, Jr. et al. | |
| 2003/0149475 A1 * | 8/2003 | Hyodoh et al. | 623/1.19 |
| 2004/0073242 A1 * | 4/2004 | Chanduszko | 606/157 |
| 2004/0116996 A1 | 6/2004 | Freitag | |
| 2006/0235463 A1 | 10/2006 | Freudenthal et al. | |
| 2008/0065146 A1 | 3/2008 | Mazzocchi et al. | |

FOREIGN PATENT DOCUMENTS

| | | |
|---|---|---|
| DE | 233303 | 12/1986 |
| DE | 4222291 | 1/1994 |
| DE | 19516060 | 11/1996 |
| EP | 0 857 471 | 8/1998 |
| EP | 1 210 919 | 6/2002 |
| WO | 98/02100 | 1/1998 |
| WO | 98/47430 | 10/1998 |
| WO | 00/44308 | 8/2000 |
| WO | 2004/047681 | 6/2004 |

OTHER PUBLICATIONS

International Search Report received in corresponding PCT Application (7 pages).
Written Opinion received in corresponding PCT Application (7 pages).

\* cited by examiner

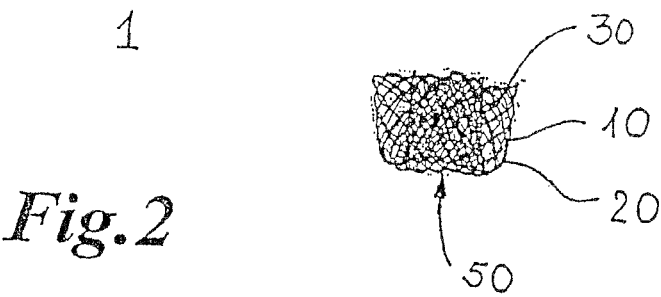
Fig.2
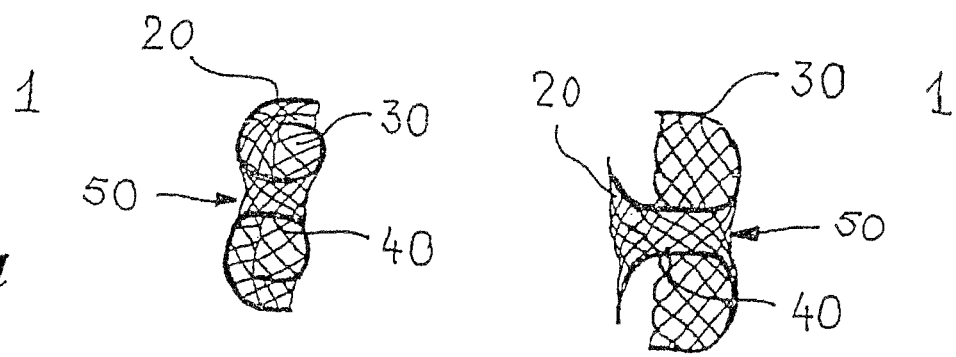
Fig.2a
Fig.2c
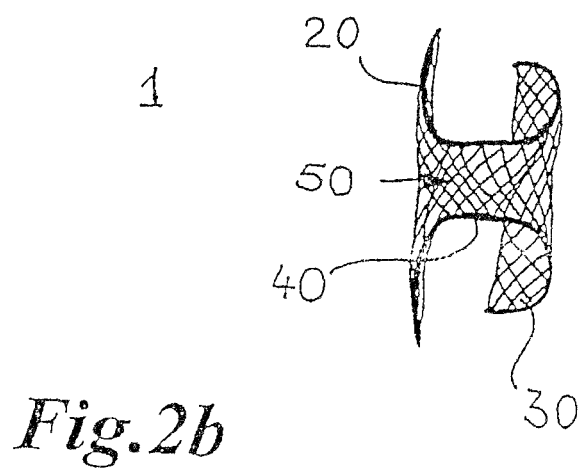
Fig.2b
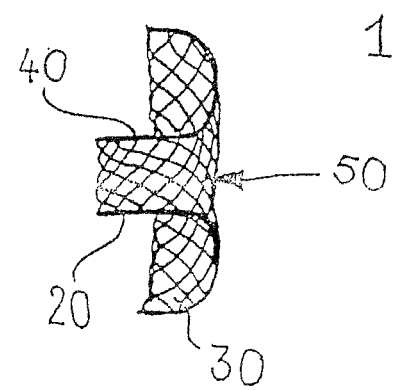
Fig.2d

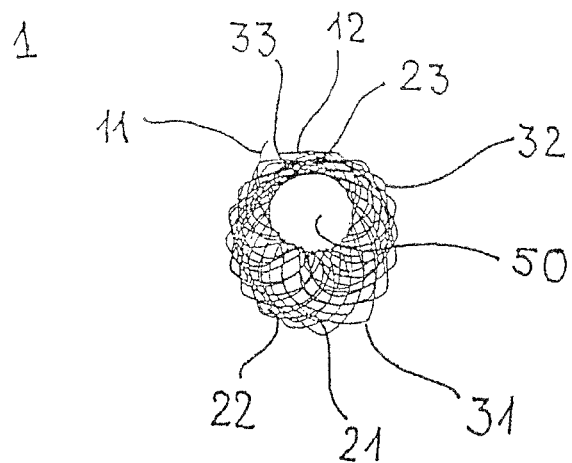
*Fig.3*
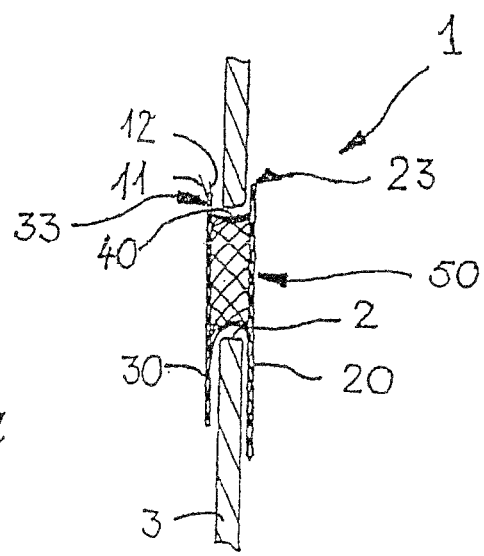
*Fig.3a*
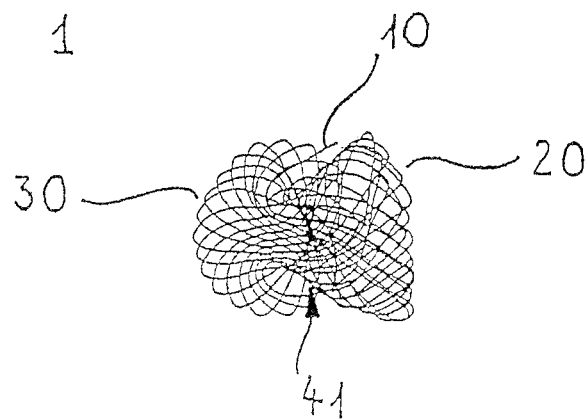
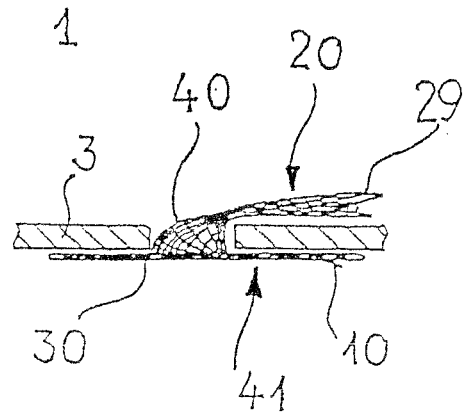
*Fig.4*  *Fig.4a*

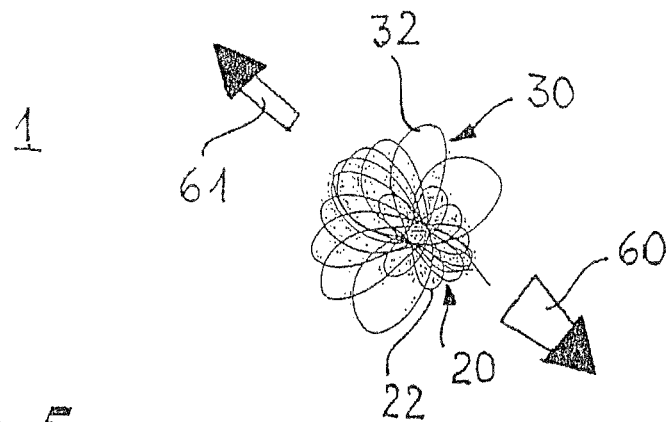
*Fig.5*
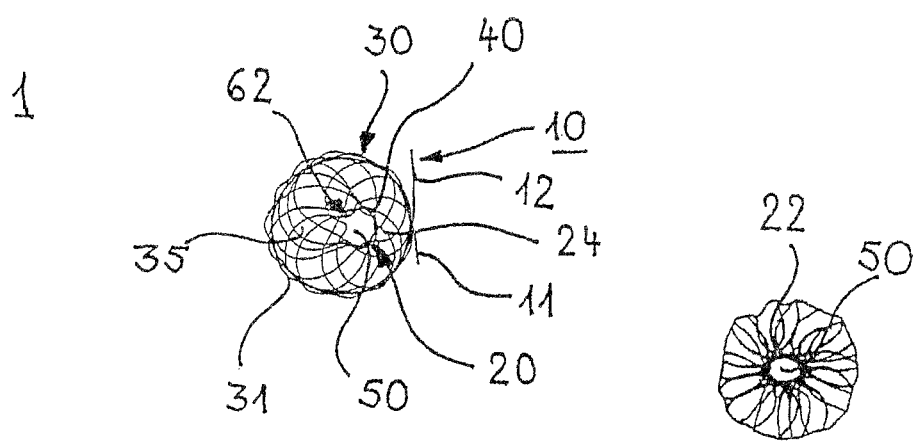
*Fig.6*  *Fig.6d*
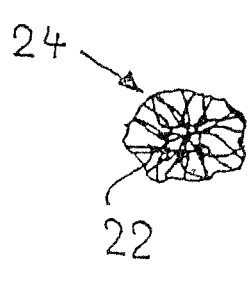 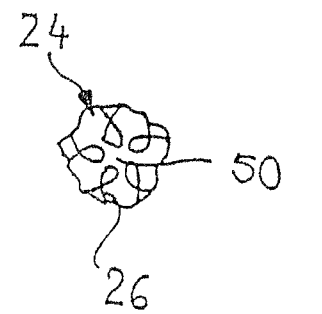 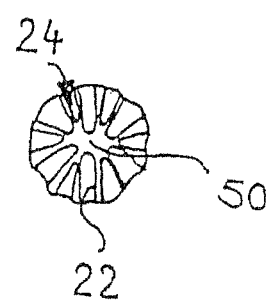
*Fig.6a*  *Fig.6b*  *Fig.6c*

IMPLANTABLE DEVICE

The invention relates to an implantable device to be used in the human and/or animal body for occluding or partially occluding defect openings, hollow spaces, organ tracts, etc. or for creating a defined connecting opening between walls, organs, hollow spaces, etc., with a support structure which has a great length-to-width ratio along an axis in a first operating state (primary shape) while having a smaller length-to-width ratio along said axis in a second operating state (secondary shape), and the support structure having a proximal portion and a distal portion.

Implants are known in the prior art. U.S. Pat. No. 5,846,261, for example, discloses a collapsible medical device which has a textile fabric made of metal, with a return piece at the proximal end and distal end of a prefabricated structure, securing means being provided at the proximal end and distal end on the textile fabric made of metal on the return piece. In the deployed state of the medical device, it presents a bell shape. The textile fabric is composed of a large number of wires which are intertwined and brought together at their ends. Also according to U.S. Pat. No. 5,725,552, a woven textile metal fabric is formed, with securing means being fitted in each case at the proximal end and at the distal end. The individual metal strands of the large number of metal strands are brought together in this securing means. In the deployed state, a bell shape is once again formed. According to U.S. Pat. No. 6,368,339 B1 and U.S. Pat. No. 6,123,715, a method is described for producing such a medical device which can be deployed in a channel or hollow space in a patient's body. In a collapsed configuration, the device can be guided through a catheter to the site in the patient's body where it is to be deployed. In this method, a textile fabric is first formed from a large number of strands which are oriented suitably with respect to one another and are made of a heat-treatable material in order to imprint a desired shape. The textile fabric is then adapted substantially to the inner surface of a shaping element, as a result of which the deployed state of the device is defined. Then the textile fabric is heat-treated in the deployed state. The textile fabric is then removed from the shaping element. The strands of the textile fabric are again brought together at a common end point at the respective distal end and proximal end of the medical device. A corresponding method is also disclosed in corresponding EP 1 210 919 A2.

The aforementioned implants are used, inter alia, for treating vascular diseases in which vessel defects are treated by minimally invasive surgery. Here, the site to be treated is not directly opened in an operation; instead, instruments and implants are introduced through relatively small incisions in the groin region or in the abdominal region. In cardiology in particular, the implants are introduced for treatment via catheters into the vessel system, in particular via the major vessels of the legs. In the treatment of septal defects of the heart, interventional procedures have, among other things, the advantage that the thoracic cage no longer has to be opened up, and the heart, which is sensitive and difficult to immobilize, no longer has to be cut open.

Further implants and catheter systems for the positioning of such an implant are described, for example, in WO 97/28744, and also in U.S. Pat. No. 5,108,420 A, DE 42 22 291 A1, DE 28 22 603 A, WO 96/01591, WO 93/13712, WO 95/27448, U.S. Pat. No. 5,433,727 A, EP 0 474 887 A1. In WO 93/13712, an implant for occlusion of septal defects is described which, in the implanted state, assumes a double cone or double disk configuration, the respective outer structures being formed from wire elements which are not connected directly to one another. These are covered with fabric membranes, said fabric membranes being sewn together in a radius corresponding to the defect to be closed. A disadvantage of this system is that the implant constructed from a plurality of structural elements requires considerable effort for its assembly.

WO 95/27448 describes an implant which is to be used as a vein filter and as a supporting structure for a septal closure. In this case, a relatively elongate double cone is formed from a series of individual devices, the cones being directed toward one another in the manner of a bone in one configuration and being made to point in the same direction, similar to a toadstool, in a further configuration.

U.S. Pat. No. 5,433,727 A discloses an implant in which a kind of umbrella is placed in front of a septal defect and is secured through the defect by a counter-closure formed essentially from four loops which are each produced by a wire and which unfold when ejected from a catheter and are intended to prevent the implant from slipping through to the umbrella side.

EP 0 474 887 A1 discloses an implant in which two round or otherwise polygonally shaped sealing patches, which are respectively stretched out by a peripheral compliant frame element, are connected inter alia by means of a multiplicity of filaments which have to be pulled tight through the catheter for the placement of the implant. A central snap closure is provided for securing the position of the two patches. The implant described in said document is very difficult to position on account of the considerable effort needed for its manipulation, and it also requires complicated assembly and is therefore very susceptible to faults.

According to WO 97/28744, an implant is described which unfolds spontaneously, on account of a secondary structure impressed on it, when it is ejected from the catheter and adapts itself within broad limits to the dimensions of the defect by means of elastic forces. The impressed structure clamps in the manner of a double disk against the surrounding region to both sides of the defect. The implant is formed by a series of wire-shaped elements which are connected to one another by suitable joining processes such as ultrasonic welding or brazing. In addition, the implant is provided with a covering which is secured on the wire-shaped elements.

DE 100 00 137 A1 discloses an implant which, in the secondary shape, assumes approximately the shape of a double disk, with a proximal disk element and a distal disk element, the surround of a defect opening being received between the disk elements, and the support structure being formed from a tube which is slit along part of its length. Along the slit part of the length of the tube, strips are formed whose width may be varied. The proximal end and distal end of the support structure are further designed as tubes, in other words the individual strips are brought together there.

DE 196 04 817 A1 proposes an implant which is built up from a plurality of wire-shaped elements and which, for more exact positioning in the patient's body, has a repositioning device at a connection point of the individual wires at one end. This repositioning device can, for example, have the shape of a ball, if appropriate with loop for receiving a guide wire, so that the screen can be better positioned at right angles to the septum wall defect and better implanted, even when the catheter is not arranged at right angles to the wall. At the other end of the wires or of the wire framework, the wire-shaped elements are connected to one another for example by another ball, a wire twist with or without eyelets, by soldering, welding, adhesive bonding, sewing, by a thread, a bushing or eyelets with or without ring.

WO 98/02100 discloses a helically wound stent for occlusion of the arterial duct with a wire which, for insertion into the human body in an extended state (primary shape), can be guided through a catheter and, inside the body, assumes an occluding state (secondary shape) in which the wire forms an occlusion anchor part and a helical anchor part and a straight connection part. In the occluding anchor part, the wire assumes the form of a series of windings which extend over the cross-sectional area of the hollow space that is to be occluded. The straight connection part is formed by the wire itself as connection between the two spirals. However, the respective spirals do not form a firm support structure, so that failure of the implant and its undesired repositioning inside the defect opening cannot be excluded.

U.S. Pat. No. 5,433,727 A discloses an implant for occlusion of large defects in large hearts, for example atrial septal defects (ASD) and ventricular septal defects (VSD). The occlusion implant comprises a foldable foam resin disk, a coated wire skeleton in the shape of an X applied to the foam disk, and an adjustable loop applied at the center of the wire skeleton.

Implants which deploy in a ball shape are also known in the prior art, for example from U.S. Pat. No. 4,994,069. Implants which coil up in a helical formation are also known, for example from DE 197 04 269 A1, or implants formed as a tube from WO 92/14408, which tube is likewise positioned in a vessel in a spiral shape or helically or wound up in loops. A further helical implant is known from WO 97/42881. A coiled implant is known from DE 32 03 410. Further helical implants are known from DE 41 04 702 A1, EP 1 046 375 A1 and DD 158 084. In all these helical implants, no firm support structure is provided. The implant according to EP 0 378 151 A2 also does not afford a firm support structure of this kind. In this, a wire bent in an undulated shape is folded into interconnected loops. By contrast, a firm support structure is formed, for example, by intertwining of a plurality of wires. In the primary or basic shape, this gives what is called a stent which, in the secondary shape, changes the length-to-width ratio along an axis, this ratio of length to width being smaller than in the primary shape (stent).

In the aforementioned implants, it has proven a disadvantage that they are either of a very complicated structure or are to be implanted in the human or animal body or that they do not permit a secure hold inside a vessel or other hollow space in the body of the human or animal. It has also proven particularly difficult to change the position of these implants if they have been incorrectly placed during the ejection procedure. In particular, the removal of the implants from the patient's body can be done only with difficulty because of their structure.

It is therefore an object of the present invention to overcome these disadvantages of the prior art and in particular to provide an implantable device which is suitable both for the occlusion and partial occlusion of an organ tract, a defect opening, a hollow space, etc., and also for creating a defined connecting opening between walls, organs, hollow spaces, etc., inside a human or animal body, that is to say can be used in a versatile way and can also be removed from the implantation site, that is to say can be implanted and then extracted.

The object is achieved by an implantable device in accordance with the preamble of claim 1, in which the support structure is formed from a single wire-like element by intercoiling and/or intertwining and/or interweaving in the manner of a tissue and/or scrim and/or net. For a positioning system for positioning such an implantable device in particular, the object is achieved by the fact that an advancing element, a guide wire and/or inner mandrel and at least one retaining wire are provided, the guide wire and the at least one retaining wire being used for cooperating with a proximal end of the implantable device, and the implantable device being transformable from a primary shape into a secondary shape and vice versa by moving the retaining wire and the guide wire relative to the advancing element. Developments of the invention are defined in the dependent claims.

Thus, an implantable medical device is created for vessel occlusion or partial occlusion of openings and other hollow spaces in the human or animal body, which device, for example, is suitable for use in VSD and ASD. Moreover, a defined connecting opening is created between walls, organs, hollow spaces, etc., inside the human or animal body. The device can be formed with great versatility using just one wire-like element. In particular, it is possible to close openings in the area of heart valves, in which area the presently known implants cannot be positioned because of the lack of space available on one side there. By virtue of the use of just a single wire-like element, the implantable device can be made of asymmetrical configuration, in particular with ends open at two sides, in contrast in particular to the aforementioned prior art in which in each case at least one end of the finished implants is closed. In these, this is due in particular to the fact that a braid or weave of numerous wire-like elements is used. In contrast to the spiral implantable devices of the prior art, in the device according to the invention a support structure is formed which is considerably more stable and which can additionally assume a very wide variety of shapes, in particular asymmetrical ones too, which is not possible in the helical or spiral implantable devices of the prior art. The support structure has considerably greater resistance to external forces and can thus be implanted in the human or animal body more safely than the spiral or helical devices of the prior art.

The support structure is preferably formed by intercoiling and/or intertwining of the wire-like element in the manner of a tissue, scrim, braid, net or the like. Despite using only one wire-like element, such a support structure can be formed by coiling, interlacing or interweaving, the support structure having a tissue, scrim and/or net structure. By means of the intercoiling and/or intertwining or interweaving of the wire-like element, a substantially tubular element is obtained in the primary shape or basic coil shape. This tubular element preferably has two open ends, the two ends of the wire-like element particularly preferably being arranged on one of the ends of the support structure or being integrated into the surface of the support structure. This results, on the one hand, in the lowest possible risk of injury to the patient in whom the implantable device is implanted and, on the other hand, an inherently secure support structure. This is not possible with the helical implants of the prior art, since their ends always end on the outer circumference of coiled disks or at the ends of the wound stents.

If the two ends of the wire-like element are woven into the surface of the support structure, they are secured against undesired loosening. If the two ends of the wire-like element end on only one of the ends of the support structure, the other end can be provided with a so-called perfect edge, that is to say a uniformly configured, substantially smooth edge, so that at this end there is advantageously no risk of injury to the surrounding tissue of the implantable device. The same can also be achieved by lacing the ends into the support structure or by their connection. Of course, it is also possible in principle that the two ends of the wire-like element protrude or are interlaced at different ends or at different positions inside the support structure and/or at one end.

The proximal portion and distal portion are preferably of disk-shaped configuration with an intermediate portion arranged between them, the intermediate portion having a reduced diameter compared to the proximal portion and/or distal portion. This configuration affords a particularly good hold in an opening inside a wall in the human or animal body, since the proximal and/or distal disk-shaped portions can gather especially effectively on both sides of the wall. Depending on how the intermediate portion is configured, either a defined through-opening can then be generated through it, or a complete or partial occlusion of the opening in the wall. Preferably, by suitable coiling, intertwining and twisting, an elongate tube with a tissue, scrim or net structure is first formed from the just one wire-like element, and this tube is then narrowed in terms of its diameter in the area between the two ends of the tube and is bent out in the area of its distal and proximal ends so that, there, a greater diameter is obtained than in the area of the intermediate portion. After imprinting of the secondary shape, which for example can be akin to a narrow tube with two very large contact disks at the ends, a substantially flat structure can be obtained. The two disk-shaped proximal and distal portions are substantially flat in a preferred embodiment; in other embodiments, however, they can also have a concave dish shape or can be bent back so far that a structure having an inner space is formed. At least one of the two proximal and distal portions in the secondary shape is preferably bent back in the direction toward the other one. Depending on the extent to which the two proximal and distal portions bent back to one another, or on the extent to which one of the two portions is bent back toward the other one, a more or less pronounced mushroom shape or bowl shape is obtained, preferably with an inner through-opening. In the secondary shape of the support structure, a central through-opening preferably remains in the implantable device for partial occlusion of an opening in the human or animal body. By means of such a partial occlusion, a defined opening can be created and, for example, a high pressure on one side of the implantable device can be decreased to a reduced pressure on the other side. An example of an area of application here is in a blood vessel leading to the head, so that high blood pressure prevailing in the blood vessel can be reduced by the implantable device before the blood reaches the head, in particular in the shoulder area. Another area of application is the pulmonary artery into which an implantable device of this kind can be inserted for partial occlusion. In addition to occlusion and partial occlusion, an open connection can also be created between two walls or between organs between which a predetermined opening is intended to remain. An application in colostomy is also possible.

A through-opening provided inside the implantable device is preferably arranged eccentrically therein. The proximal portion and distal portion can be offset from one another, so that the intermediate portion, and in particular the through-opening, is not arranged centrally in the implantable device, but instead away from the center. This proves advantageous precisely when using the implantable device for occlusion of openings in the area of heart valves, if a defined through-opening or the intermediate portion between the proximal portion and distal portion is arranged in the edge area of the implantable device. In this way, despite the lack of space on one side, the device can be implanted firmly and safely. The arrangement of the through-opening and of the intermediate can be chosen depending on the field of application of the device.

The dimensions and shape of the implantable devices, of a through-opening inside the implantable device and/or of the edge of the implantable device can preferably be selected or adjusted specifically to the application. The position of the through-opening inside the implantable device or support structure can also be selected specifically to the application. It can for example also be formed on one side in the edge area of the device. The amount of material in the edge area of the implantable device can particularly preferably be adapted to the desired properties, in particular a concentration of material being provided in the edge area of the device for partial stiffening. If an implantable device according to the invention has the maximum diameter preferably in the edge area of the proximal portion and/or distal portion, this area is especially suitable for adjusting and changing the stability of the implantable device in a targeted manner. If a uniform concentration of material is generated across the surface of the implantable device, the latter has substantially the same flexibility throughout and thus also the same deformability. If a firm hold is to be generated for example inside a blood vessel or inside another duct in the human or animal body, the edge area of the support structure can be made particularly stable by a material concentration there. By contrast, in the area of the remaining surface of the support structure, a greater flexibility and bendability is then maintained. If in particular a defined passage is to be created inside a blood vessel or another duct inside the human or animal body, an annular shape as secondary shape can be formed from the tubular primary shape or basic coil shape, in which case in particular the entire material is concentrated only in the edge area, so that a very stable ring is into this ring, so that an occlusion of an opening is possible by this means too. It is precisely by virtue of the material concentration in the edge area that a so-called "perfect edge" can be formed there. The latter is characterized by the fact that it is substantially plane, that is to say no hoops or loops protrude there. In this way, a particularly good and less injury-intensive hold is possible within ducts, in particular blood vessels or other organ tracts in the human or animal body.

At least a partial area of the implantable device is preferably designed folded in or is able to be folded in. In this case, the proximal portion and distal portion of the support structure in the secondary shape are preferably placed flat and partially on top of one another so that an occlusion or partial occlusion of openings delimited laterally by walls, especially in the area of valve flaps, is possible in the human or animal body. In the primary shape or basic coil shape of the implantable device, the latter is preferably once again configured as a tube, and only in the secondary shape is it folded in either just on one side or at several places, such that any desired shapings are possible, the entire implantable device or support structure preferably being of a flat configuration in the secondary shape. However, it is also possible only for partial areas, namely those folded onto one another, to be designed flat. By means of the folding-in, in particular one-sided folding-in of a part or all of the support structure, configurations are possible which can also be positioned in locations that are not otherwise accessible with conventional implants. In this connection, it proves particularly advantageous that the entire implantable device can be substantially flat.

In addition, asymmetrical and/or irregular configurations are possible at least in e portion of the support structure in the primary and/or secondary shape. Therefore, there no longer has to be a rotation symmetry, as is customary in the implantable devices of the prior art and is in principle essentially only possible as a result of their structure. In this case, it is particularly preferred that the material concentration and/or the material thickness inside the support structure is different from portion to portion. The wire-like element can thus itself have different material thickness, that is to say a different diameter. Alternatively or in addition, the provision of more than the one wire for forming the support structure is possible, which wire can be partially doubled or strengthened. In this way too, material concentrations can be specifically achieved at certain locations, such that the support structure is made partially stiffer or less stiff. The range of variability is wide, since, for a particular application, a defined shape can be specifically set and, in terms of its stiffness, likewise adapted to the specific application. If only an asymmetrical structure can be accommodated at the distal end or proximal end, it is also possible to design one portion in such a way that no extent or substantially no extent of the support structure in one direction is achieved, whereas the other portion has an extent in each direction. Thus, at least at one end, a particularly good hold can be generated in an opening which, on the other end, has no space for a uniformly configured implant.

The end of the proximal portion is preferably open or partially closed or completely closed, in particular by provision of a plate element. Since the support structure is formed from only one wire-like element, the end of the proximal portion preferably has one or more hoops or loops which are arranged alongside one another and/or interlocked and/or interlaced. Here, a substantially uniform edge can also be formed if the hoops or loops are interlocked lengthwise. Such an edge is suitable precisely in disk-shaped proximal and distal portions. For example, if the proximal portion forms a short stub inside the surface of the distal portion, the proximal portion preferably has hoops or loops at its end. These surround a through-opening, in which case they can be preferably designed as e-shaped loops alongside one another or as u-shaped hoops alongside one another or interlocked for exactly delimiting the through-opening or in the one and/or other form interlocked or interlaced so that in the latter case the through-opening is substantially closed. A complete occlusion can take place in particular by means of a securing plate as plate element. This can be added, for example bonded on, sewn on, welded on, etc., or worked in, there for example by threading through the hoops at the end of the proximal portion for example.

Preferably, the distal portion and/or proximal portion is substantially flat in a disk shape or ring shape or at least bent round in the edge area or bent back toward an intermediate portion connecting the distal and proximal portions, so that a delimited inner space is formed. Depending on how far the proximal portion or distal portion is bent round or bent back, a structure is formed which, in a side view, is cup-shaped or may even be a structure which is completely bent back at one side or at both sides (proximal and/or distal) and whose end(s) protrude(s) into a central through-opening. By means of the distal and/or proximal portion bent back in this way, an inner space is in each case formed there, while at the same time, however, the advantage of a substantially flat configuration is maintained. Of course, by pulling the distal portion and/or proximal portion apart, it is also possible to bring about an enlargement in the direction of the axis passing transversely through the implantable device. This too can be set variably, depending on the application.

The support structure is preferably designed as a two-part or multi-part unit connected to one another to form one part and formed from a wire-like element. However, it can equally well consist of a structure continuously coiled in one part. Particularly preferably, the individual parts of the support structure are designed uniformly, corresponding to one another or differing from one another. By virtue of the fact that a continuous tube or similar element is preferably not formed, but instead various parts which are chained together, substantially without an interruption between the individual parts, a greater stiffness of the support structure can be achieved. In addition, a special additional stiffening is possible in the area of the chaining together of the parts. In addition, the individual parts can be differently configured, in which case gaps between the individual parts are partially possible. In this way, upon shaping into the secondary shape, special effects can again be produced, in particular asymmetric secondary shapes can be generated. In addition, support structures can be produced with a stiffness that differs over the cross section. If such a support structure similar to a stent in the primary shape or basic coil shape were designed with distal loops and openings or gaps in the structure, this could also be used to capture objects in organ tracts or body organs or openings. The individual portions of the basic coil shape can also have different coil angles, as a result of which differently stiff areas can likewise be produced.

One or more membranes or membrane-like or membrane-forming structures are preferably incorporated into the support structure or applied to it. The membrane-forming structure is preferably formed by inweaving of at least one filament, in particular a filament made of a flexible weavable material, in particular a plastic, a renewable raw material or metal. It is particularly advantageous for Dacron filaments to be woven into a support structure made of nitinol and/or for a weave, scrim, braid or the like to be formed from these filaments and introduced into the support structure. Alternatively or in addition, carbon fibers are also suitable. By means of these fibers or filaments, a through-opening extending through the implantable device can be closed. Through the provision of membranes, membrane-like or membrane-forming structures in the support structure, a complete occlusion of, for example, defect openings in the body of a human or animal can be generated. Depending on the design and arrangement of the membrane inside the support structure, a partial occlusion can also be created in this way. As has already been mentioned above, such a membrane can also be incorporated into an annular secondary shape of the support structure, or a membrane-forming structure, such that, depending on the flexibility of the membrane or membrane-forming structure, a construction is obtained which moves flexibly to a certain extent but which is introduced firmly in an organ tract. Such introducible membranes can be prefabricated textile scrims, weaves, braids or the like and can even be integrated into the wire-like element of the support structure woven to the support structure. A combination of both possibilities is also possible. For example, a subsequent threading of at least one filament to form a membrane structure is possible. The filament or the material of the membrane-forming structure preferably differs from that of the wire-like element, but it can also have the same cross section. The membrane-forming structure is preferably made of a material with a thinner cross section or has a braid, scrim or weave with filaments of different diameter. To create different impermeabilities inside the membrane-forming structure, the filament or the material of the membrane-forming structure preferably has different diameters, or several filaments guided in parallel are provided. The membrane-like structure can alternatively preferably be formed by dipping the support structure into a film-forming material. Such a material can in particular be a natural or synthetic polymer formed from one or more monomers, in particular formed by polyaddition, polymerization or polycondensation, in particular a polycarbonate, polyester, polyamide, polyolefin or polyurethane. Polystyrenes are also suitable. Depending on the application, a material is preferably selected which has a greater or lesser flexibility or surface tension and in particular does not trigger rejection processes in the human or animal body. Depending on whether something, e.g. tissue, is intended to gather on the membrane-like structure, the material selection can be in the direction of hydrophobic or hydrophilic materials. A coating of the membrane-like structure and/or of filaments of a membrane with such materials is also possible.

The membrane-like structure or membrane is preferably formed from a weave, scrim or other textile and is provided in the edge area with protruding arms for threading and/or securing on the support structure, in particular by sewing, adhesive bonding, welding, crimping, or another securing method. In this case, the protruding arms are routed in particular around the edge area of the support structure at the distal end and/or proximal end and attached to the surface of the membrane-like structure or membrane and secured there. A particularly good hold, secure against slipping, on the support structure is possible in this way.

The membrane or membranes and membrane-like or membrane-forming structure(s) is/are preferably arranged proximally and/or distally and/or substantially centrally in the support structure. The membrane(s) and membrane-like or membrane-forming structure(s) can also be arranged obliquely inside the support structure that is to say for example, from the proximal to the distal side if this appears appropriate to the specific application. An only partial arrangement of these inside the support structure is also possible, in particular in order to permit a partial occlusion.

In a further preferred form, the implantable device can be formed from a cut tube. In this case, the tube is likewise cut in such a way that a stent open at both ends is in particular formed in the primary shape, which stent, in the secondary shape, can be designed as described above, in particular also asymmetrically and irregularly. The provision of the support structure formed from one wire-like element is replaced by the tube section. In principle, this simulates the wire-like element coiled correspondingly to give the tissue or scrim or net of the support structure.

Preferably, the material of the support structure is chemically and/or mechanically treated in at least a partial area, in particular etched, electropolished, microground or otherwise treated. In this way it is possible to generate different material thicknesses and, therefore, different stiffnesses. Such treatment is particularly suitable in a cut tube. The wire-like element or cut tube of the implantable device is particularly preferably made of a biocompatible material, in particular a metal or a metal alloy, in particular a high-grade steel or shape-memory material such as nitinol or a plastic such as polycarbonate, for example. A material is preferably used with which it is possible to configure different primary and secondary shapes, these being impressed into the material in such a way that, when the implantable device is positioned inside a human or animal body, the secondary shape is automatically adopted or a desired change between the primary shape and the secondary shape is possible, in particular using further auxiliary means. To permit compatibility with the animal and/or human body; a biocompatible material is used in particular. From polycarbonates, it is possible, particularly by laser cutting, to form tissue-like, scrim-like or net-like structures. By application of a suitable film material, a membrane, as described above, can also be provided on such a support structure. A greater flexibility is possible with a laser cut than with intercoiling or intertwining of a wire-like element. In particular, a support structure formed from a polycarbonate also has a good foldability characteristic. This makes transport to the implantation site especially easy. The same applies to carbon fibers. The support structure can be produced from these, in particular also by sewing. By dipping the produced support structure in polyurethane, a shape-memory structure can likewise be formed. By using carbon fibers or polycarbonates, it is possible to dispense with the use of metals, some of which are not so well tolerated by the patients.

The position of the implantable device during an implantation procedure may advantageously be detected by X-ray or by 3D ultrasound. When using a metal material for the support structure of the implantable device, X-ray detection may advantageously be performed, whereas, when using a polycarbonate to form the support structure and/or Dacron filaments and/or carbon fibers to form a membrane or membrane-like structure, 3D ultrasound is suitable for detection purposes.

For positioning the implantable device inside the human or animal body, a positioning system is preferably provided. In this, the retaining wire or retaining wires is/are preferably threaded or can be threaded through one or more loops or hoops at the end of the proximal portion and can be connected to the guide wire and/or inner mandrel. Application of the retaining wires at the distal end is also possible.

In particular, a retaining wire can be threaded through all loops or hoops at the end of the proximal portion. In an alternative embodiment, for example, two retaining wires can be threaded through all or several loops or hoops at the end of the proximal portion which are arranged in a half thereof, in which case the guide wire or inner mandrel preferably extends through a loop between the two retaining wires, which is formed by these, such that the retaining wires have a securing point there. When the guide wire or inner mandrel is pulled back out of this loop, the retaining wires can then also be pulled back so that the proximal portion can unfold completely in this area. Alternatively, several retaining wires can also be threaded through several hoops or loops at the end of the proximal portion, in which case the retaining wires are preferably always threaded only through some of the hoops or loops. It is possible here for any desired number of retaining wires to be provided, in particular also one retaining wire per loop or hoop, in which case a chain of retaining wire loops is preferably formed and the guide wire or inner mandrel is preferably pulled through only one loop at the end of the chain of wire loops.

If all loops or hoops at the end of the proximal portion are brought together, it may suffice to provide just one retaining wire with one loop, and a guide wire or inner mandrel which is guided through this loop. For example, 1, 2, 10, 12, 18, 24 or any other desired number of loops or hoops can be formed at the end of the respective proximal or distal portions, through which any desired number of retaining wires can be threaded.

For positioning the implantable device at a site inside the human or animal body, use is preferably made of a catheter and an advancing tube, in particular a guide wire and a retaining wire or retaining wires. First, the loops or hoops at the end of the proximal portion and in particular also of the distal portion are threaded by means of the one retaining wire or several retaining wires, and the guide wire is positioned such that the retaining wire is fixed therein, so that premature loosening from the implantable device is thus substantially avoided. The advancing tube is then positioned via guide wire and retaining wires, and the implantable device is drawn into the advancing tube, whereupon it adopts an elongate shape. The catheter is introduced into the patient's body, the advancing tube preferably being already introduced into the catheter or being introduced into it afterward. The catheter is advanced until it is positioned in the area of the site where the implantable device is to be released. Thereafter, the advancing tube and then the guide wire are pushed out of the catheter together with the implantable device, after which they are pushed out of the advancing tube and released at the site where it is to be positioned.

With the positioning system according to the invention, it is likewise possible also to extract an implantable device back out of the patient's body. This may be sensible or indeed necessary either after incorrect positioning or when healing has taken place. For this purpose of extracting the implantable device from the implantation site in the human or animal body the positioning system according to the invention is preferably provided with a guide wire and an extraction wire, the extraction wire being able to be made into a hoop and able to be threaded through at least one hoop or loop at one end of the support structure. For the extraction procedure, at least one hoop of the at least one extraction wire is preferably first passed through the implantable device. The guide wire is likewise passed through the implantable device and also through the hoop of the extraction wire. By pulling on the extraction wire and on the guide wire, the hoop secures itself on the guide wire, at any rate if guide wire and extraction wire have not taken the same route through the implantable device. By pulling on both wires, the implantable device can be drawn into a catheter and, if appropriate, completely removed from the implantation site. Repositioning is also possible in this way.

A set of several differently shaped implantable devices is preferably offered, together with at least one retaining wire and/or extraction wire, in which both can be identically designed, with a guide wire and/or inner mandrel and, if appropriate, with a catheter. In particular, the catheter and the retaining wire or extraction wire and the guide wire and/or inner mandrel can also be used several times, whereas the implantable device usually remains in the patient.

Alternatively or in addition to the positioning system described above, it is possible for such a system to have an advancing element, an auxiliary structure having a great length-to-width ratio along an axis in a first operating state (primary shape) while having a smaller length-to-width ratio along said axis in a second operating state (secondary shape) for aiding the deployment of the proximal end of the support structure, and at least one connection device for connecting the proximal end of the implantable device and the distal end of the auxiliary structure. The provision of such an auxiliary structure can afford a remedy if problems arise upon deployment of the proximal end of the support structure. At its distal end, the auxiliary structure is connected to the proximal end of the support structure and is brought, together with the latter, to the implantation site, for example via a catheter. After deployment of the distal end of the support structure, the proximal end of the support structure and the distal end of the auxiliary structure connected thereto are deployed. The distal end of the auxiliary structure is configured in such a way that, upon its own deployment, it also deploys the proximal end of the support structure. By use of such a positioning system, the support structure can be positioned precisely, and in such a way that, after its release, substantially no more movement is permitted. The connection device preferably has at least one retaining wire, in particular three retaining wires. To connect the two structures, the use of one retaining wire is already sufficient. When using three retaining wires, spreading and removal are possible almost without force. The at least one retaining wire is preferably threaded or can be threaded through one or more loops or hoops at the end of the proximal end of the implantable device and of the distal end of the auxiliary structure. This permits a good connection between the structures on the way to the implantation site and simple removal of the at least one retaining wire after spreading of the proximal end of the support structure.

Preferably, the ends of the wire-like element are suitably connected to one another in order to reduce the risk of injury to the patient. A sleeve or a tubular element is particularly preferably fitted onto the ends and is secured there in particular by pressing or adhesive bonding. In addition, another element such as a spiral or similar can be fitted onto the two ends. Direct connection, in particular by welding, soldering, twisting or adhesive bonding or the like, is also possible.

The implantable devices according to the invention can thus satisfy different functions. They can, on the one hand, be introduced through a catheter into the patient's body in order to permit occlusion or partial occlusion or to provide a defined through-opening. They do not interfere with other structures inside the patient's body, are implantable and remain in place independently after release at the implantation site. Nevertheless, if they do cause interference or if they have been incorrectly positioned, they can be removed again from the implantation site. Implants have hitherto been provided with a support framework in order to be stable. The implantable devices according to the invention have sufficient stability through their shape alone and, as a result of this, can also be brought independently to the desired position. They no longer have to be made symmetrical, and they can therefore be designed specifically in accordance with the implantation site and can position themselves there in the correct orientation.

Figure 1A:
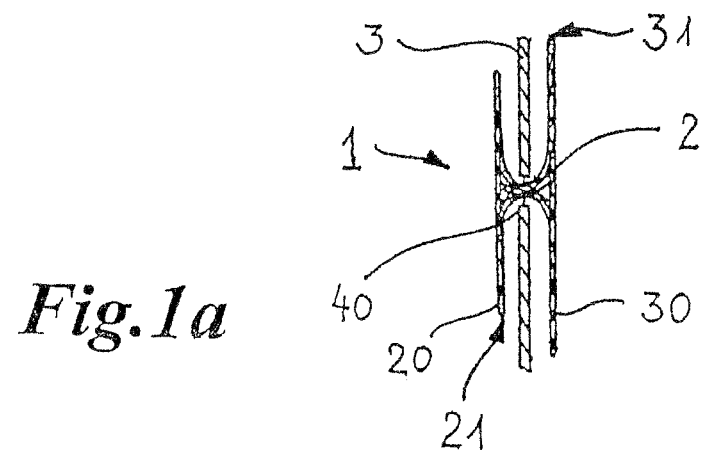
Figure 7:
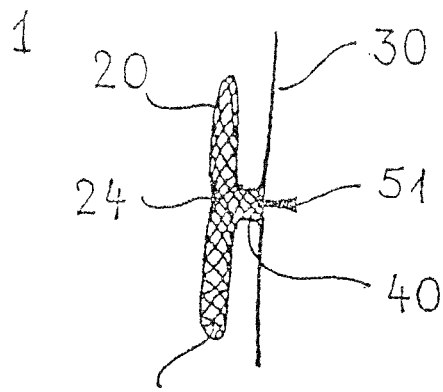
Figure 7A:
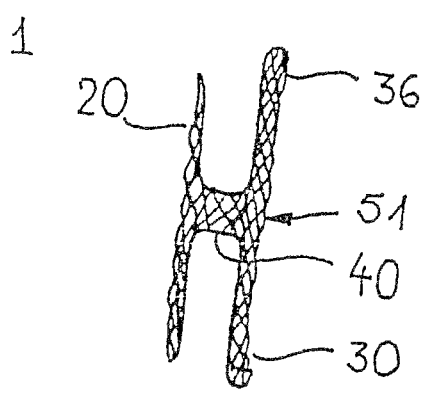
Figure 7B:
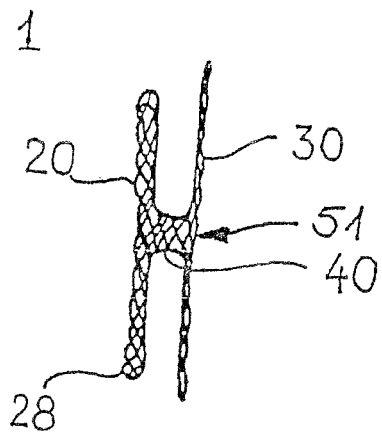
Figure 7C:
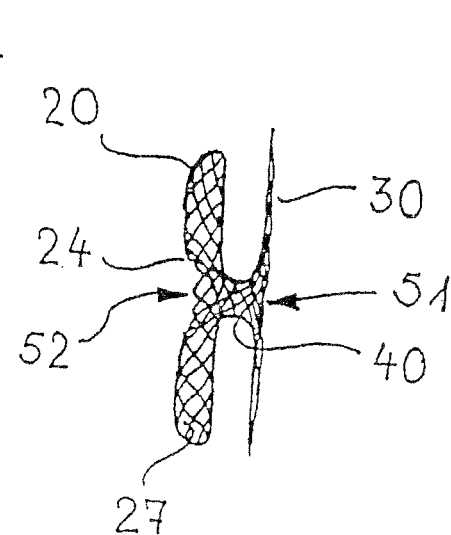
Figure 8A:
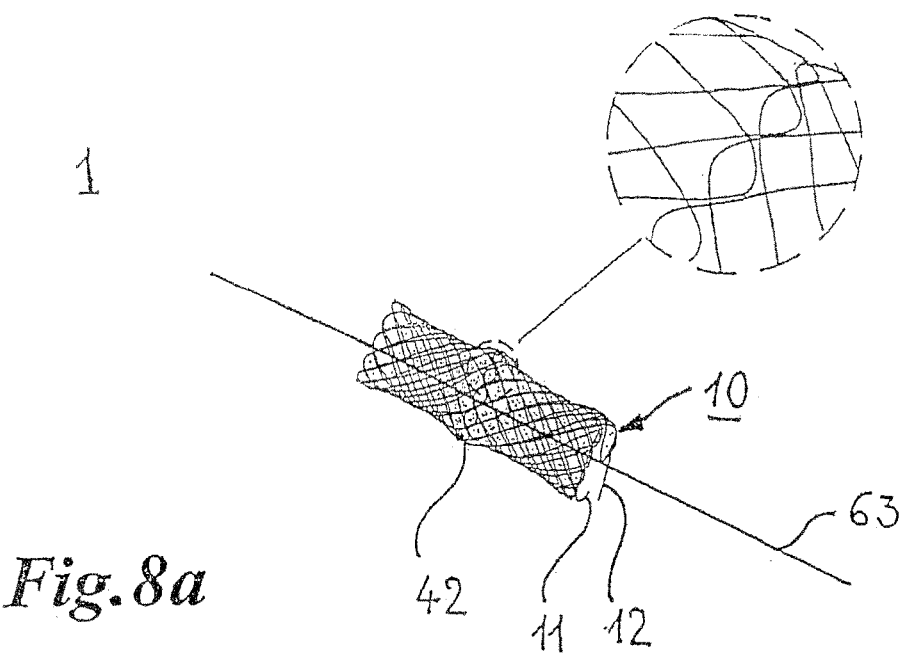
Figure 8B:
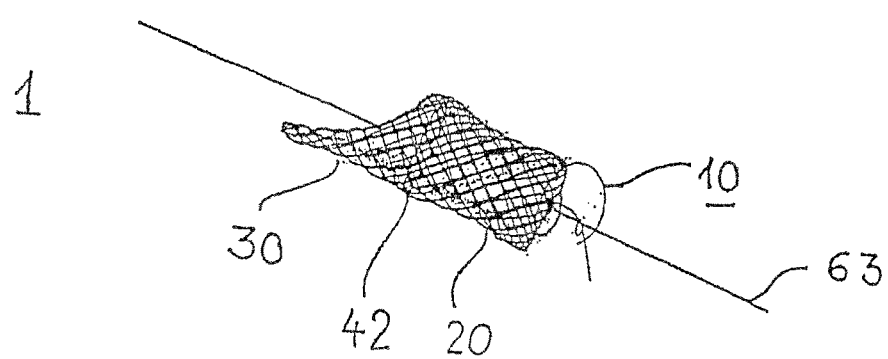
Figure 8C:
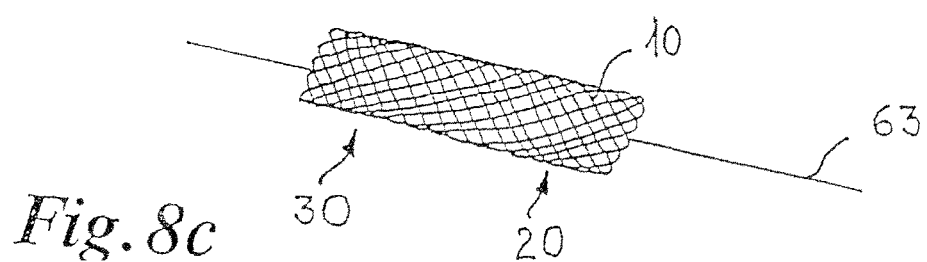
Figure 8D:
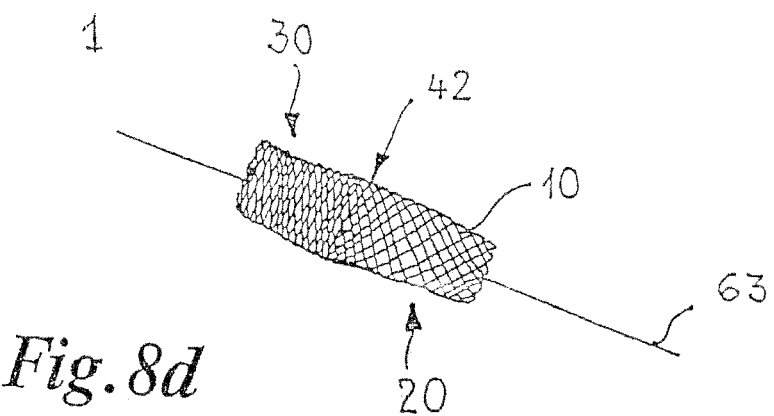
Figure 8E:
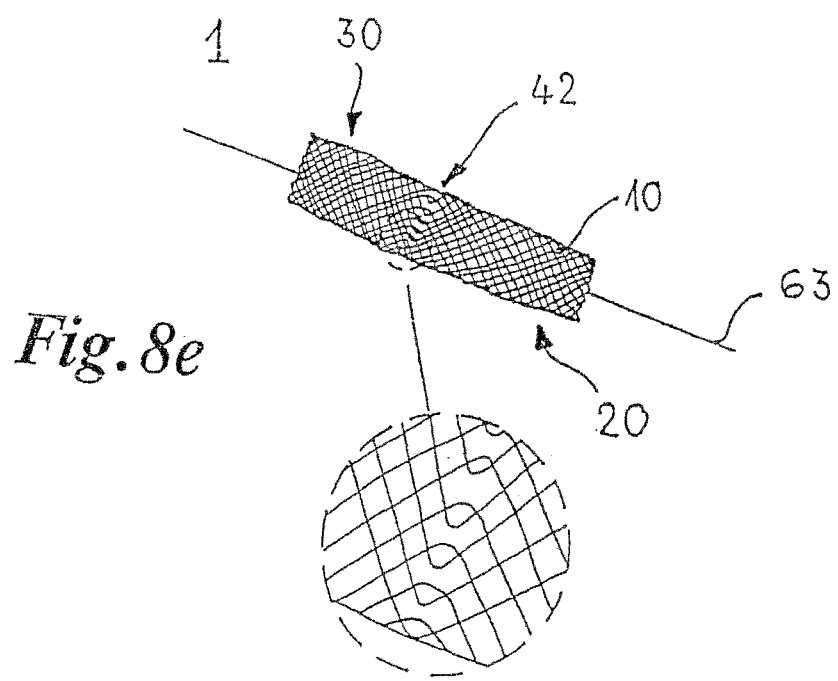
Figure 12B:
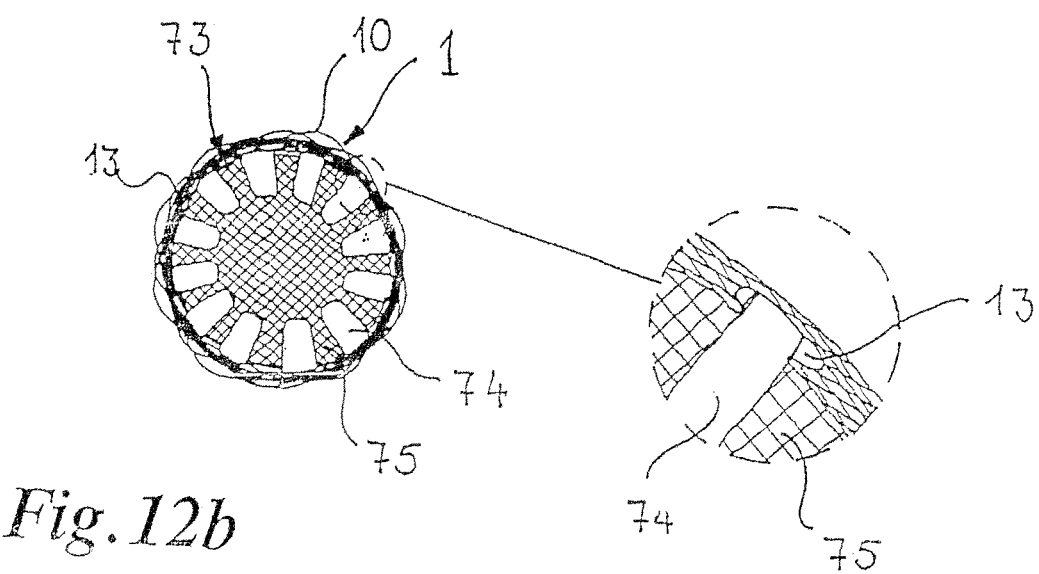
Figure 9:
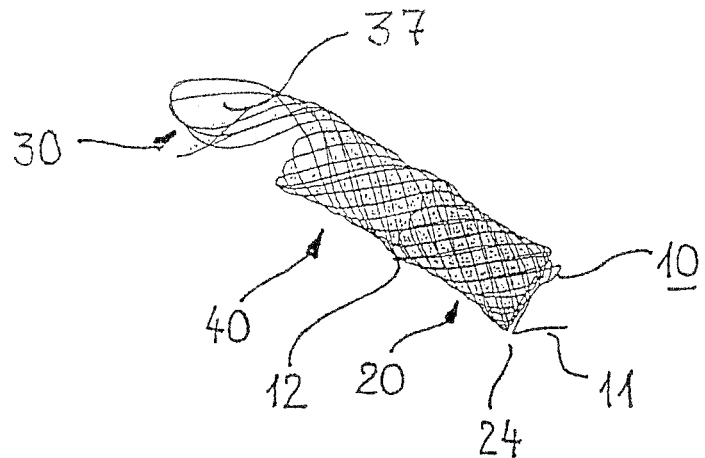
Figure 10A:
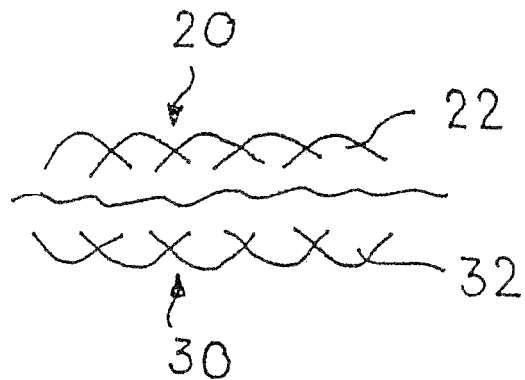
Figure 10B:
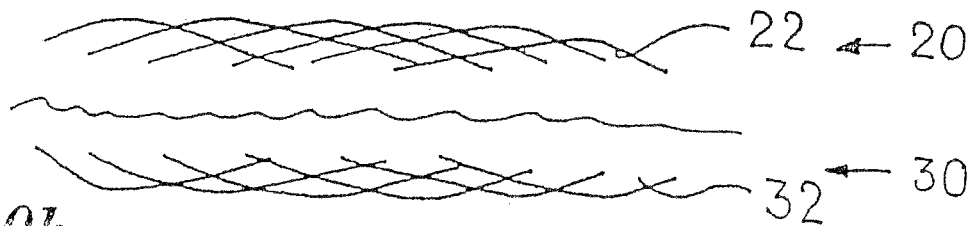
Figure 10C:
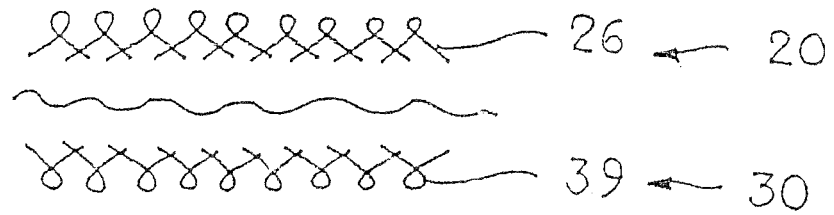
Figure 11A:
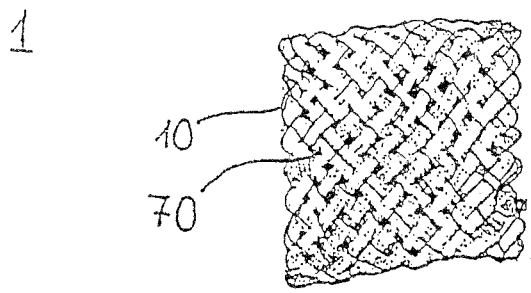
Figure 11B:
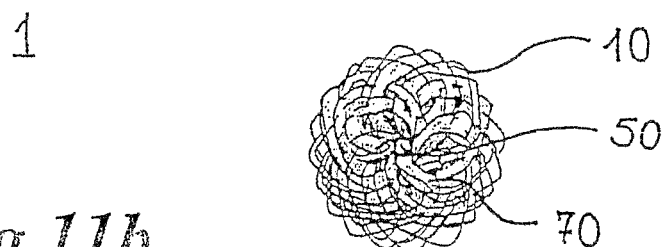
Figure 11C:
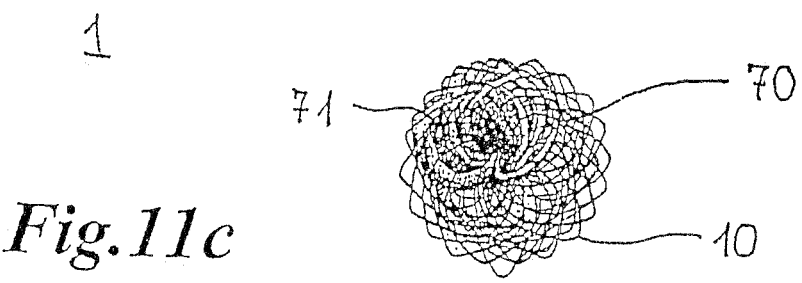
Figure 11D:
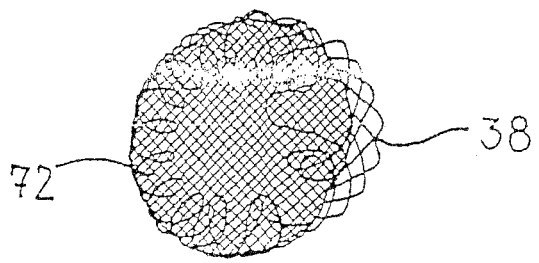
Figure 11E:
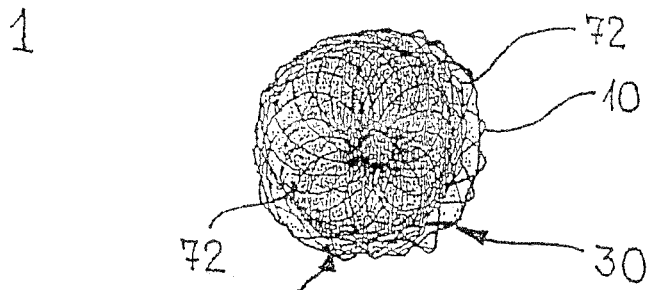
Figure 12:
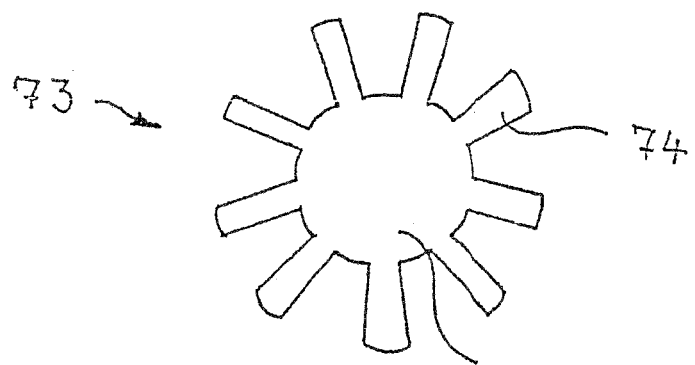
Figure 12A:
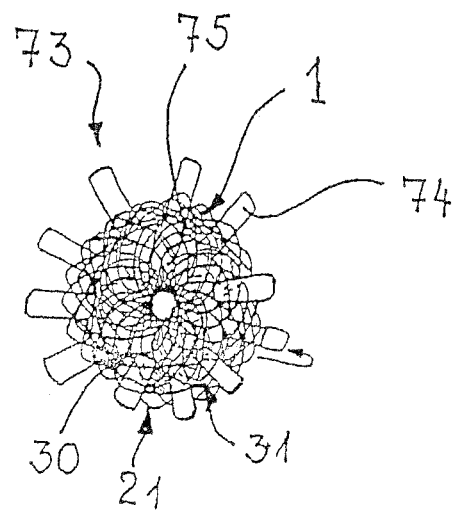
Figure 13A:
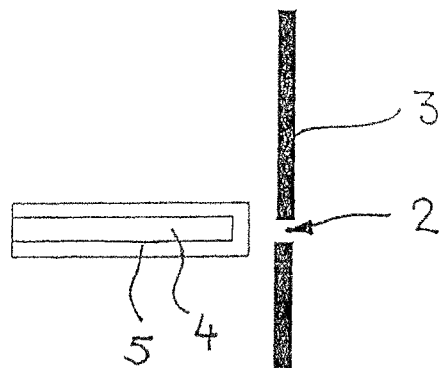
Figure 13B:
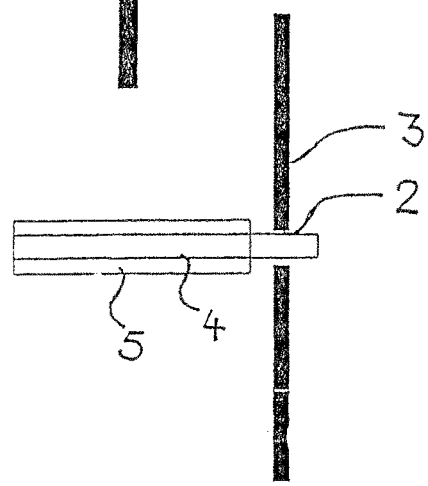
Figure 13C:
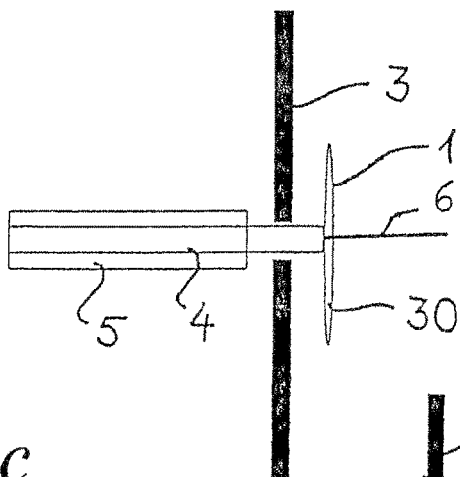
Figure 13D:
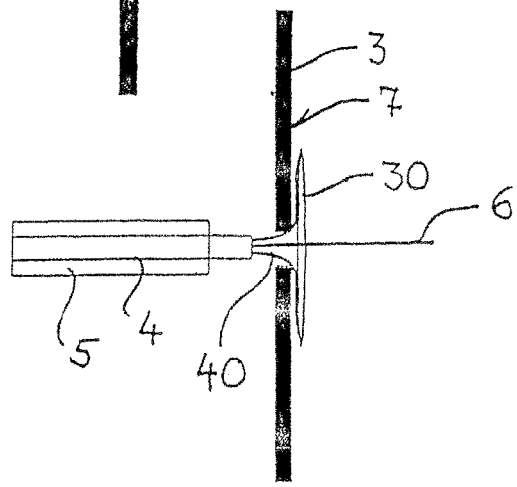
Figure 13E:
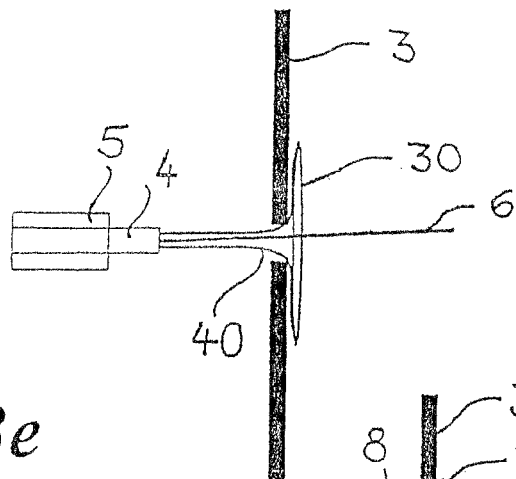
Figure 13F:
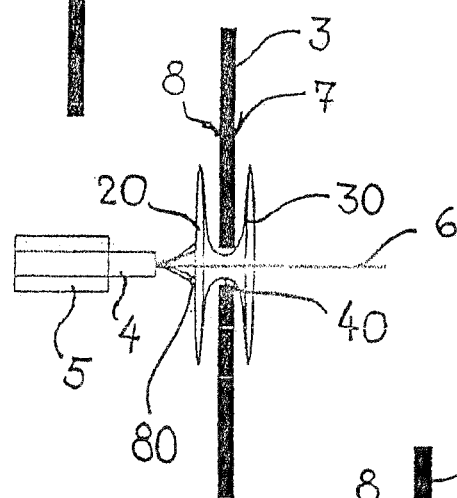
Figure 13G:
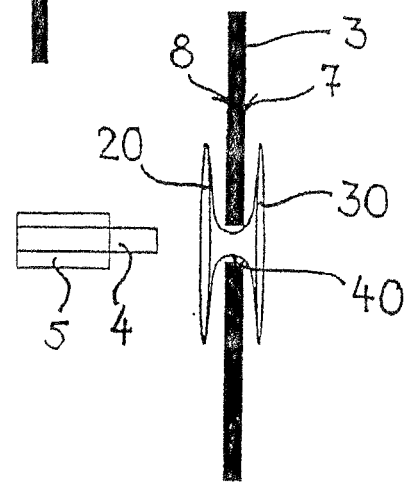
Figure 14A:
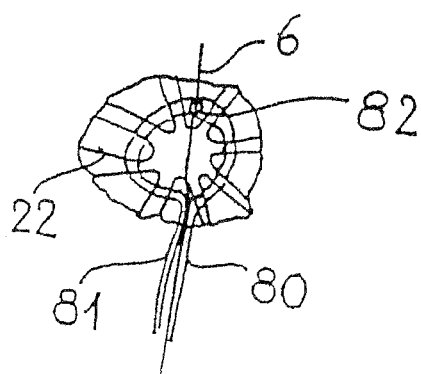
Figure 14B:
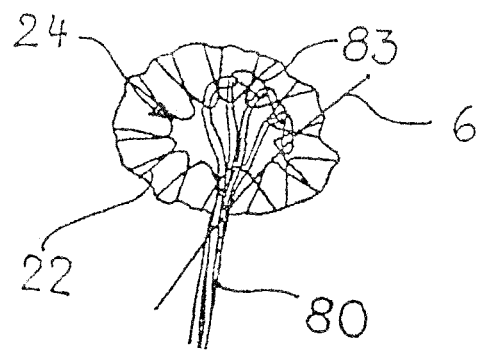
Figure 14C:
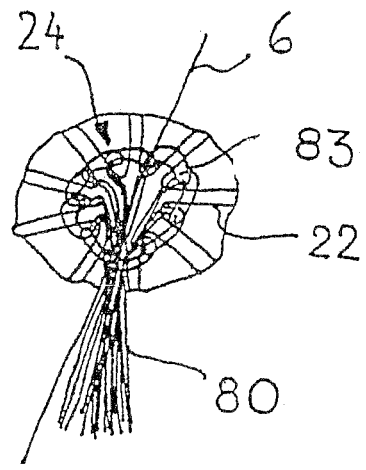
Figure 15:
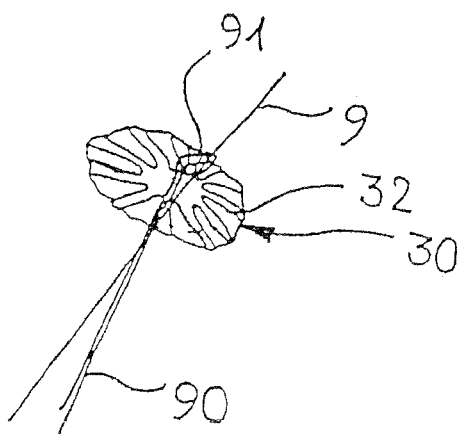
Figure 16:
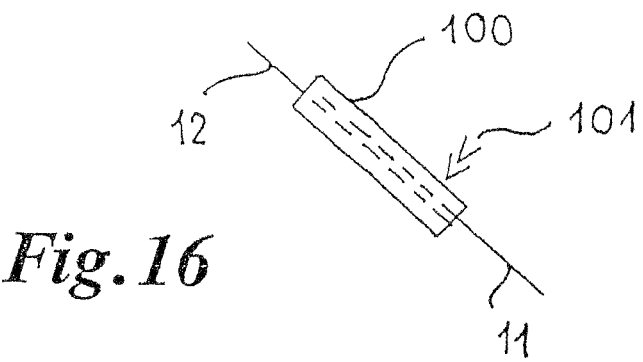
Figure 16A:
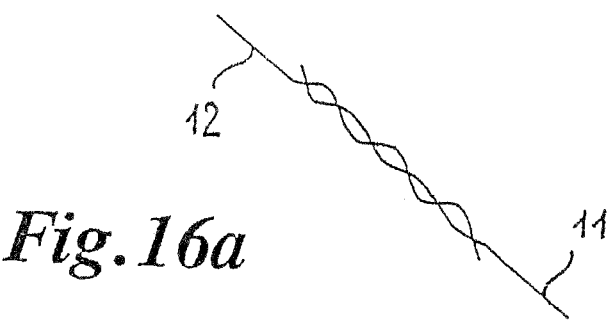
Figure 16B:
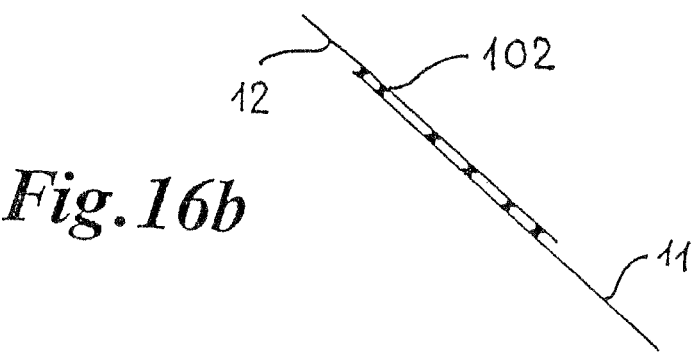
Figure 16C:
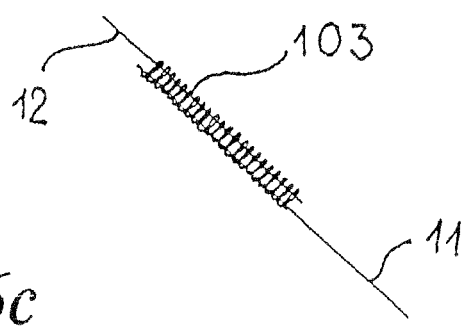
Figure 17A:
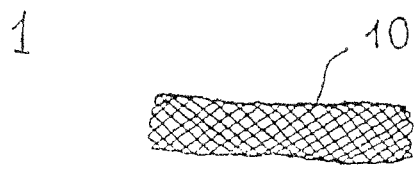
Figure 17B:
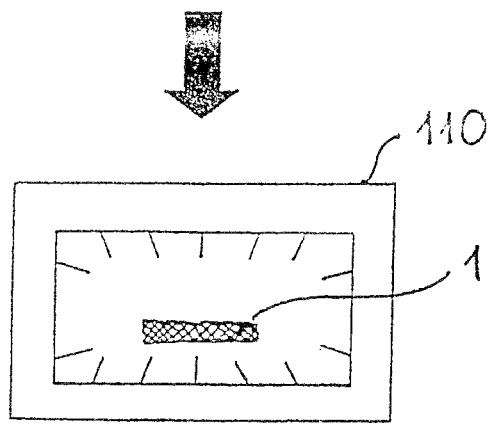
Figure 17C:
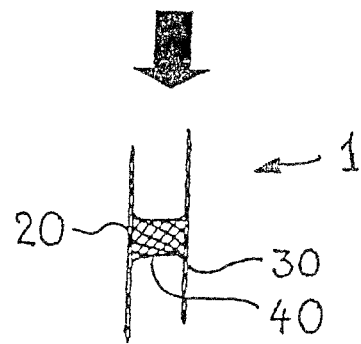
Figure 17D:
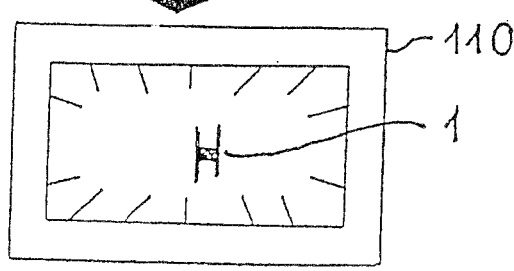
Figure 17E:
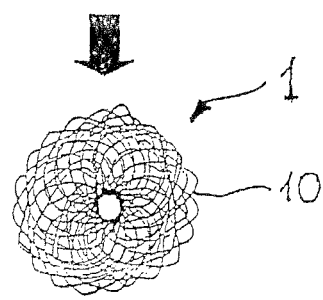
Figure 18A:
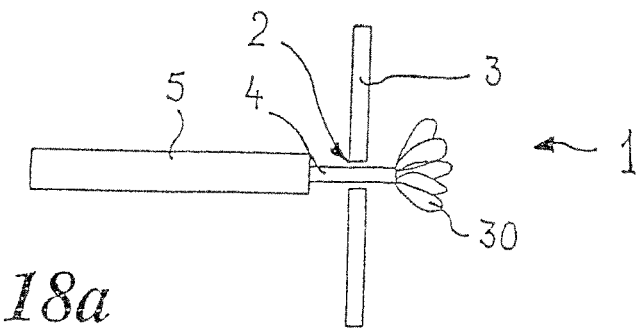
Figure 18B:
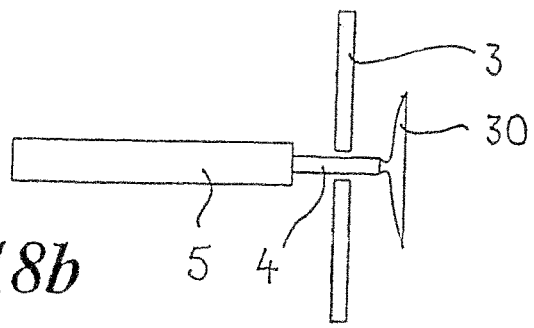
Figure 18C:
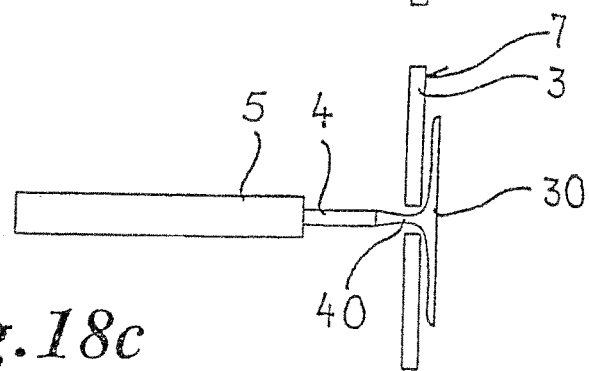
Figure 18D:
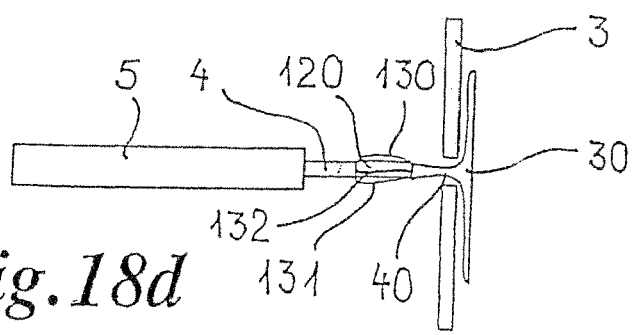
Figure 18E:
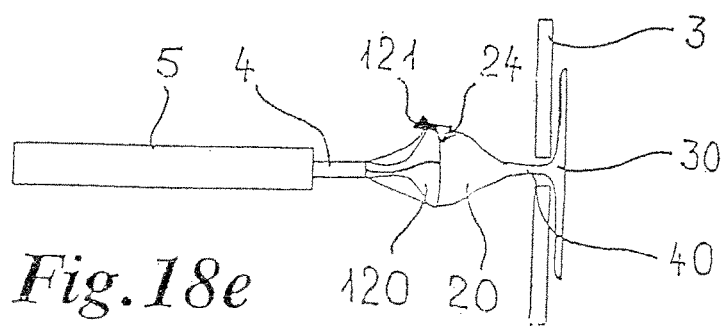
Figure 18F:
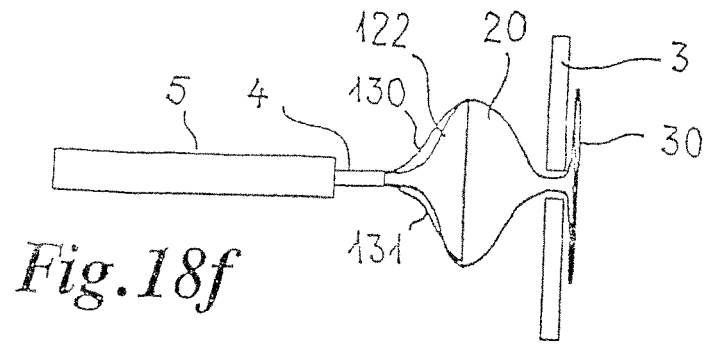
Figure 18G:
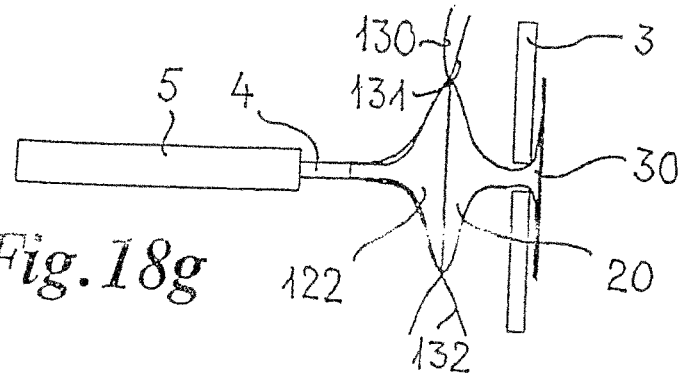
Figure 18H:
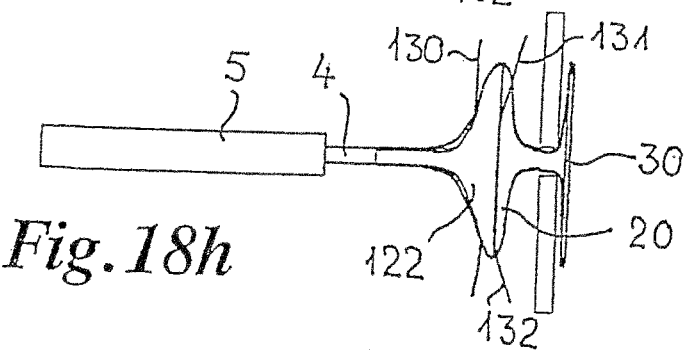
Figure 18I:
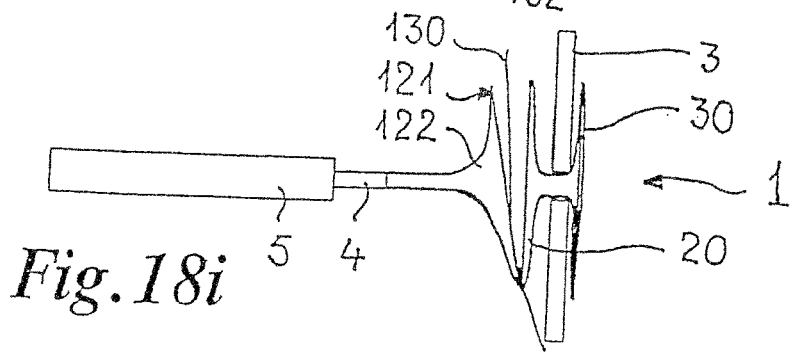
Figure 18J:
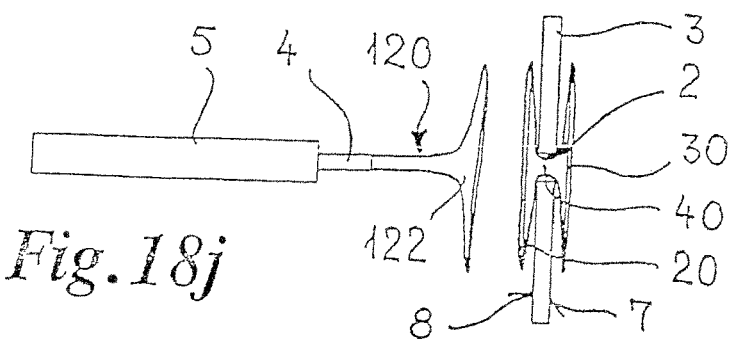
Figure 19A:
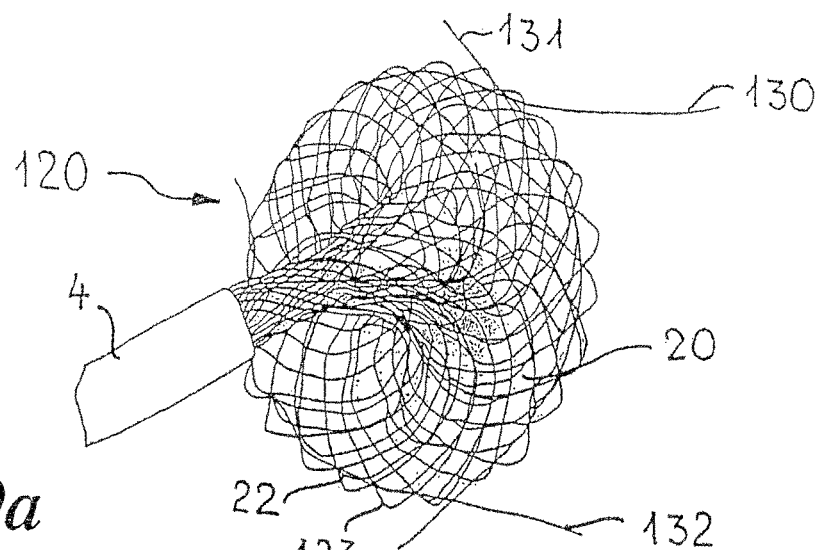
Figure 19B:
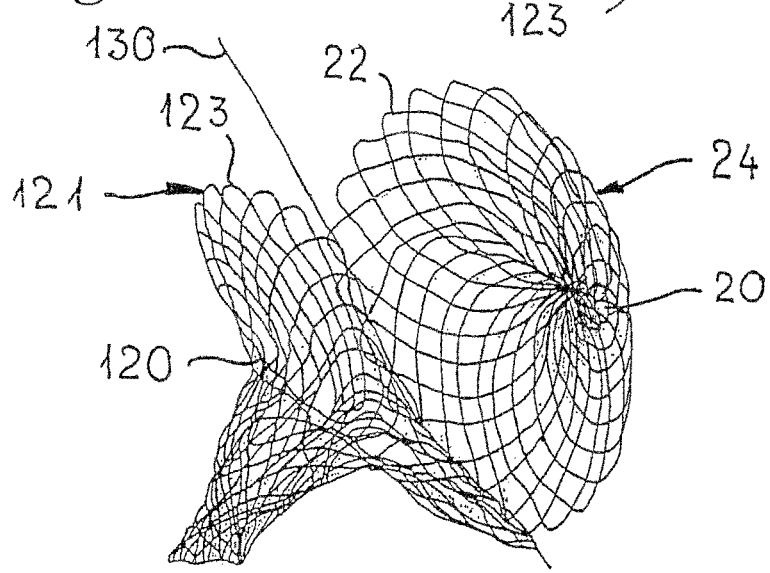

For a more detailed explanation of the invention, illustrative embodiments are described in detail below with reference to drawings, in which:

FIGS. 1, 1a show a plan view and lateral plan view of a first embodiment of an implantable device according to the invention, FIG. 2 shows a plan view of a second embodiment of an implantable device, FIGS. 2a to 2d show sectional views of various further embodiments of a modification of the embodiment according to FIG. 2, FIGS. 3, 3a show a plan view and side view of a further embodiment of an implantable device in which a through-opening is arranged asymmetrically, FIGS. 4, 4a show a plan view and side view of a further embodiment of an implantable device according to the invention which has a folded-in partial area, FIG. 5 shows a plan view of a further embodiment of an implantable device according to the invention which has an irregularly configured distal portion, FIG. 6 shows a plan view of a further embodiment of an implantable device according to the invention with an edge area of the distal portion with material concentration and with a proximal portion which is very short and has loops lying alongside one another at the end, FIGS. 6a to 6d show detailed views of further variants for forming the proximal portion of the implantable device according to FIG. 6, FIG. 7 shows a plan view of a further embodiment of an implantable device according to the invention, with the proximal portion bent back toward the intermediate portion, FIGS. 7a to 7c show further variants of the embodiment according to the implantable device according to the invention in FIG. 7, FIGS. 8a to 8e show side views of embodiment variants of basic coil shapes of an implantable device according to the invention which is formed in two contiguous parts from only one wire-like element, FIG. 9 shows a further embodiment of an implantable device according to the invention in which it is composed of several parts on or in one another, only one wire-like element being used, FIGS. 10a to 10c show schematic views of various configurations of the edge area of a distal portion, FIGS. 11a to 11e show plan views of various embodiments of implantable devices according to the invention which are provided with membranes or membrane-like or membrane-forming structures, FIG. 12 shows a plan view of a further embodiment of a membrane for an implantable device according to the invention, FIGS. 12a, 12b show plan views of membranes according to FIG. 12 introduced into support structures, FIGS. 13a to 13g show the sequence involved in positioning an implantable device according to the invention, FIGS. 14a to 14c show detailed views of ends of proximal portions of implantable devices according to the invention in which retaining wires and guide wires of a positioning system according to the invention are arranged, FIG. 15 shows a detailed view of an end of an implantable device according to the invention with extraction wire and guide wire, FIGS. 16 to 16c show plan views of embodiments of end attachments of the ends of a wire-like element, FIGS. 17a to 17e show a schematic representation of the sequence involved in production of an implantable device according to the invention, FIGS. 18a to 18j show a schematic representation of the sequence involved in an alternative embodiment of the positioning of an implantable device according to the invention, FIGS. 19a and 19b show perspective views of two steps involved in positioning by means of the positioning system according to FIGS. 18a to 18j, and FIG. 20 shows a schematic view of retaining wires being threaded through in the positioning system according to FIGS. 19a and 19b.

FIG. 1 shows a plan view of a first embodiment of an implantable device 1 according to the invention. It is made up of two disk-shaped proximal and distal portions 20, 30 and an intermediate portion 40 arranged between these. A through-opening 50 is provided inside the intermediate portion. As can be seen from FIG. 1a, which presents a lateral plan view of the embodiment according to FIG. 1, the two proximal and distal portions 20, 30 are not each arranged symmetrically with respect to the intermediate portion but instead are offset with respect to one another and to said intermediate portion. The through-opening 50 is therefore not arranged centrally in the two proximal and distal portions. The intermediate portion 40 is formed by dividing two parts from a tubular primary shape of the implantable device 1 by winding or twisting, namely the proximal portion 20 and the distal portion 30. The proximal and distal ends of these portions are thereafter drawn out and bent until the disk-shaped portions are obtained. Because only one wire-like element 10 is used for the entire implantable device, loops 22, 32 are formed in the outer edge area 21, 31 of the distal and proximal portions. These loops can also be used for the threading-through of retaining wires during positioning at the intended site inside a human or animal body where the implantable device is to exert its function, namely that of complete or partial occlusion of defect openings, hollow spaces, organ tracts, etc., or a defined connecting opening between walls, organs, hollow spaces, etc. As is indicated in FIG. 1a, the implantable device 1 positions itself and deploys after release in such a defect opening 2, for example in a wall 3 in the human heart.

The embodiments of an implantable device 1 shown in FIGS. 2 and 2a to 2d differ from that shown in FIG. 1 in particular in that they are not so flat and in addition can be implanted especially effectively for reducing pressure in vessels. The embodiments shown in these figures are likewise all made from a single wire-like element 10. In the embodiment shown in FIG. 2, the proximal portion 20 is bent back in the direction of the distal portion 30 so that a collar shape is formed with an inner through-opening 50. The distal portion here is substantially cylindrical. The second half of the proximal portion also extends substantially cylindrically. Upon implantation into a vessel or another tubular organ, only a partial occlusion is created, it still being possible for blood, for example, or for another body fluid to pass through the through-opening 50.

In the embodiment according to FIG. 2a, both the distal portion 30 and also the proximal portion 20 are bent toward one another. In this way a flatter structure is obtained than in FIG. 2. The extent to which the distal portion and the proximal portion are bent toward one another can be chosen for the specific application. Because of the two ends of the distal portion and proximal portion being bent toward one another, a still better spring action in the transverse direction in this area is possible and therefore, upon introduction into a vessel, a still better hold is created than is possible with the embodiment according to FIG. 2 for example. The embodiment according to FIG. 2b has a substantially flat proximal portion 20 and a distal portion 30 bent toward it. The through-opening 50 once again remains between the two, the intermediate portion 40 being longer and more cylindrical than in FIG. 2a. In this embodiment, in terms of the circumferential lateral extent, the proximal portion extends beyond the distal portion or the circumference formed by the end of the distal portion.

In the embodiment shown in FIG. 2c, the distal portion is again bent round to the proximal portion, but the intermediate portion 40 is shorter than in the embodiment according to FIG. 2b, and the proximal portion is not bent out substantially in a disk shape, but only slightly bent so that it describes a smaller circumference and diameter than the end of the distal portion. The embodiment shown in FIG. 2d essentially represents a reversal of the embodiment shown in FIG. 2, since in this embodiment according to FIG. 2d the distal portion 30 is bent back to the proximal portion 20, but the proximal portion remains substantially cylindrical.

From FIG. 2 and FIGS. 2a to 2d it will be apparent that numerous variants are possible in which the distal portion and/or the proximal portion is bent back respectively to the other one, with an inner through-opening 50 remaining between the portions. It is thus possible in particular to effect a partial occlusion or an open connection of defined diameter between two walls or inside a vessel. In all the embodiments represented in FIGS. 2 to 2d, a particular force is in each case provided for securing the device 1 in the patient's body, which force at the same time is sufficiently elastic to ensure that moving organ tracts or vessels can be provided with such an implantable device 1 without there being any risk of it moving in an undesired manner inside the vessel or organ tract. Rather, the implantable device 1 stays particularly firmly in place therein.

FIGS. 3 and 3a show a further embodiment of an implantable device 1. FIG. 3 shows a plan view and FIG. 3a a side view of the device 1 in a state in which it is inserted into a wall. The through-opening 50 is arranged eccentrically in the edge area 21, 31 of the proximal portion and distal portion. The proximal and distal portions lie substantially flat and more or less congruently over one another. The edge area 23, 33, which is directly adjacent to the through-opening 50 to the side of the proximal portion and the distal portion, is made with a greater concentration of material. This means that in this area the mesh width of the loops or meshes formed by the wire-like element is smaller, such that these edge areas 23, 33 are stiffer than the remaining edge areas 21, 31 of the distal portion and of the proximal portion.

It will be seen from FIG. 3 that the through-opening can be arranged at any desired site in the implantable device, that it can also have any desired variable diameter, that the concentration of material can also change over the cross section of the implantable device, in particular of the proximal portion and distal portion, especially in the edge area, and that the mesh width and the circumference and size of the proximal portion and distal portion can be adapted variably to the particular application. In particular, compared to FIG. 1, it will be evident that the diameter of the through-opening 50 in FIG. 3 is larger, such that a partial occlusion is formed when fitted in a defect opening or the like in the human or animal body.

However, as will be explained in more detail below, each of the through-openings represented in the preceding figures and in the following ones can be more or less closed with a membrane or a membrane-like or membrane-forming element or such a structure. In this way, a complete occlusion is then also possible despite the large through-opening.

As can also be seen in particular from FIG. 3, an edge can be formed by loops 22, 32 and/or an edge designated as a "perfect edge" in which the individual loops are placed very tightly over one another and, in the case represented in FIG. 3, a higher concentration of material is also thereby obtained in the edge area 23 and 33. In this way, it is possible to partially modify the mechanical properties of the edge area and thus also of the entire implantable device 1. As can be seen in particular in FIG. 6, a ring area can also be formed all round the entire implantable device, which ring area has a high concentration of material and thus a greater stability than the remaining area of the implantable device.

A further embodiment of an implantable device is represented in FIGS. 4 and 4a. In this embodiment, a partial area 29 of the proximal portion is folded in, such that a very flat structure is formed. On the proximal side, the portion situated there thus lies doubled. Between the proximal portion and distal portion, in a cover area 41, there remains a gap-shaped partial piece into which, for example, a wall 3 can be introduced in order to secure the implantable device thereon (see FIG. 4a). Despite the fact that the implantable device is very flat, a complete occlusion of a defect opening or the like is possible, because the intermediate portion 40 is closed on the proximal side (FIG. 4a). For example, this embodiment is also suitable for introduction in the area of a heart valve since the device 1 can be folded in in any desired way in the proximal and/or distal portion so as to permit optimum adaptation to the small space available on one side in the area of a heart valve. The extent to which the proximal portion and/or distal portion is in each case folded in can therefore be dependent on the particular application. Completely irregular support structures may be formed which can then be optimally adapted to the spatial conditions in each case.

In the embodiment shown in FIG. 5, an irregular support structure is likewise formed. In its upper area, this plan view shows the distal portion 30 and, in its lower area, it shows the proximal portion 20. The distal portion is formed almost exclusively from loops 32. However, these loops are arranged only in an area covering approximately 250° of the circumference. In the remaining circumferential area, there is no such loop. Matters are different with the proximal portion. In FIG. 5, the latter has loops 22 in the area indicated generally by the arrow 60. Toward the side in the direction away from the arrow 60, and indicated in FIG. 5 by the arrow 61, only a few loops 22 are formed in the proximal portion. It is thus possible to permit particularly good securing of the implantable device 1 in the proximal area. In the distal portion, the lack of a loop or loops in the area 60 permits adaptation to a possibly protruding organ or any other obstacle in the human or animal body, while, however, an optimal hold is also possible on the distal side because the distal portion permits good securing in the direction of the arrow 61.

FIGS. 6, 6a, 6b, 6c and 6d show further embodiments of the implantable device according to the present invention, FIGS. 6a to 6d in each case showing only details of the proximal portion. The securing side or actual securing side is once again the proximal end 24. This is very short in FIG. 6 and basically represents only a slightly extended intermediate portion 40 surrounding the through-opening 50. The distal portion is provided in the edge area with a "perfect edge". The wire-like element 10, from which the support structure of the entire device 1 is again formed, is shown protruding here. The end 11 of the wire-like element 10 protruding from the edge area 31 is also woven in there. For illustration purposes, however, it is pulled out here. The other end 12 of the wire-like element 10 is preferably likewise woven into this edge area or alternatively into the surface 35 of the distal portion.

In the embodiment shown in FIG. 6, the proximal end 24 is formed with loops engaging adjacently over one another. In an area 62, only three loops are arranged alongside one another without being interlocked in the edge area or covering one another. The edge area of the proximal portion is therefore also irregularly configured here. Alternatively, however, it can also be configured regularly, as is indicated for example in FIG. 6c. Here, the loops 22 are each arranged alongside one another. Alternatively, e-shaped hoops 26 can also be formed, as is indicated in FIG. 6b. These too can be arranged alongside one another or engaging over one another. A defined through-opening 50 is generated by the embodiment according to FIG. 6d in which the loops engage over one another and delimit the opening 50. Both in the embodiment according to FIG. 6b and in the embodiment according to FIG. 6c or 6d, a through-opening 50 still remains. However, if the individual e-shaped hoops 26 or loops 22 are completely interlocked, no through-opening remains in the center or in the interior of the proximal portion and therefore also of the distal portion (FIG. 6a). In this area, a securing plate can in addition be fitted in order to ensure a better securing inside an opening in the human or animal body. The securing plate can, for example, bear on a side of a defect opening. In this way, a complete occlusion of an organ tract, of a defect opening or the like is then also made possible.

In a further alternative embodiment, only the edge area of the distal portion and of the proximal portion remains. Such a ring is to be seen as a support structure for a membrane in FIG. 12b. The proximal portion is drawn out so far that it lies in the diameter area of the distal portion. This results in a very stable ring which can be provided with an inner membrane or can also be fitted as stiffening means, without such a membrane, into an organ tract or the like in the human or animal body.

FIGS. 7, 7a, 7b and 7c show further embodiment variants of the proximal portion 20. The distal portion is in each case of a substantially disk-shaped configuration. However, in an alternative embodiment, it can also be configured according to the proximal portions. FIG. 7 shows a side view of an embodiment of a proximal portion which is first drawn out in a disk shape and is then bent back in and, at the proximal end 24 in the area of the through-opening, has interlocked ends of loops and hoops. A through-opening 51 is here formed only in the area of the distal portion 30 and of the intermediate portion 40. It ends inside an inner space 27 formed by the proximal portion 20.

The embodiment according to FIG. 7c differs from the one according to FIG. 7 in that the proximal end 24 of the proximal portion 20 is not completely closed, i.e. the loops and hoops terminating there do not cover one another, and instead leave an opening 52 between them. An inner space 27 is furthermore delimited by the proximal portion. The through-opening 51 beginning in the distal portion 30 continues through the intermediate portion 40 into the opening 52 in the proximal portion. If the openings are not closed by a membrane, a partial occlusion is now possible after implantation of this device 1.

A still better passage of fluids is made possible by the device 1 represented in FIG. 7b. In this, the edge of the proximal portion, i.e. the proximal end, is not drawn together as far as the through-opening. Instead, the proximal portion is simply formed by first being pulled out in a plate shape from the intermediate portion 40 and then being drawn slightly in again at the edge. This edge area 28 is akin to a hat brim. An inner space is no longer delimited, or only in this edge area. An in this respect still more extreme form is shown in FIG. 7a. Here, the proximal portion is again bent out substantially only in a plate shape and only very slightly proximally outward. The distal portion is likewise bent out slightly in the distal direction. This can also be done differently about the circumference of the distal portion, as is indicated in FIG. 7a in the edge area 36. Here, only a partial piece of the edge is folded inward or formed into a brim, so that a brim is formed along part of the circumference of the distal portion.

FIGS. 8a to 8e each show variants of basic coil shapes of the support structure of an implantable device 1 according to the invention. The respective basic coil shapes are substantially tubular and, when only one wire-like element 10 is used, constructed from two halves placed onto one another in an attachment area 42, the two halves are joined to one another, in each case further using only the one wire-like element 10. A greater stiffness of the basic coil shape is thus achieved in this attachment area 42. In certain applications this may prove particularly advantageous since a good hold is possible in this area even after the reshaping to the desired secondary shape. For example, by simple pushing together in the direction of the longitudinal axis 63, an annular support structure can be obtained in FIG. 8a with, in the edge area, loops engaging over one another, both on the proximal side and on the distal side. In the area between the proximal side and the distal side or their ends, that is to say in the attachment area 42, a collar of protruding loops likewise extends from the ring. These subsequently projecting loops of the chained ends of the affixed halves can be seen particularly clearly in the detail in FIG. 8a. In addition, numerous other configurations are possible as secondary shapes, such as are shown, for example, in the above figures and in those described below. According to FIG. 8a, the two ends 11, 12 of the wire-like element are guided out on one side from the tubular basic coil shape.

FIG. 8b represents a variant of FIG. 8a, the second half of this device being formed only on one side, i.e. the wire-like element 10 is coiled here in such a way that the in this case distal portion 30 is formed only in part starting from the attachment area 42. Conversely, the partially coiled area can also be the proximal portion. Any other desired configurations can also be obtained here. For example, both portions 20, 30 can be formed only in part. The configuration here depends in particular on the particular application and on which secondary shape is to be obtained. If so desired, stiffening can be provided in the attachment area 42 by suitable coiling, so that a good hold is permitted at the implantation site.

FIG. 8c shows a symmetrical configuration of the basic coil shape, i.e. both halves, that is to say proximal portion 20 and distal portion 30, are coiled symmetrically with respect to one another. The coiling is preferably done in one pass, without formation of two halves. A further variant is shown in FIG. 8d, where two halves worked onto one another from a wire-like element are provided as basic coil shape. The two halves, that is to say the proximal portion 20 and distal portion 30, each have different angles in respect of the direction of coiling. The angle in the distal portion 30 is in this case approximately 180°, whereas the coiling angle in the proximal portion is approximately 90°. Of course, any other desired angle values are possible. In the attachment area, these two halves are fitted on one another to form one piece, with only one wire-like element 10 being used for the entire basic coil shape.

A further variant is shown in FIG. 8e. Here, the two halves of the basic coil shape, which form the proximal portion 20 and distal portion 30, are fitted on one another such that, in the coiling process, a reversal of the direction of coiling is provided in the attachment area 42. This can be better seen from the detail in FIG. 8e. In this way too, as has already been mentioned in the embodiment according to FIG. 8d, special effects can be achieved, particularly in respect of the stiffness of the secondary shape of the support structure; in particular, only partial stiffening can be provided in the support structure.

FIG. 9 represents a further variant of such a support structure of a device 1 composed of several parts. The first part, here for example the proximal portion 20, is cylindrically shaped, while the intermediate portion 40, although substantially cylindrically shaped, has a number of gaps. The distal portion 30 consists only of four interconnected loops, so that large openings 37 remain there. If the device is used for capturing objects inside the human body, for example stones, etc., these openings can be used for example to grip and secure these objects. This embodiment according to FIG. 9 shows that any desired individual portions, which together are all formed from just one wire-like element, can be fitted on one another. The two ends 11, 12 of the wire-like element are then preferably guided out on only one side, in particular at the proximal end of the proximal portion. In this way, the risk of injury to the patient can be limited to the best possible extent. Alternatively, however, the ends can also be woven into the jacket surface, for example of the proximal portion, or of the other portions.

FIG. 10 shows, in its parts a, b and c, possible formations for edges of the distal portion and proximal portion. Here, the loops 22, 32 can each be interlocked with their adjacent loops (FIG. 10a), crossed lengthwise over by the adjacent loops (FIG. 10b) or can be e-shaped (FIG. 10c). Numerous intermediate forms are also possible. The choice of the edge shape can be made depending on the specific application.

FIG. 11a to lie show different embodiment variants of implantable devices 1 according to the invention which have membranes, membrane-forming or membrane-like structures. FIG. 11a shows a lateral plan view of a tubular basic coil shape of an implantable device 1 produced from just one wire-like element, where a further filament 70 is woven into the support structure of the device 1. Since the material thickness of the wire-like element 10 and of the filament 70 differ very greatly from one another, the filament 70 being much thicker than the wire-like element, an especially tight membrane-like structure can be formed. When a primary shape, such as is represented in FIG. 11a, is transformed into a secondary shape, the variant shown in FIG. 11b may be obtained, for example. The latter is substantially identical to the one shown in FIG. 1. In contrast to this, however, the variant shown in FIG. 11b is substantially impermeable to liquid, particularly also in the area of the through-opening 50, since the filament 70, by being woven with the wire-like element, forms a membrane. Depending on the choice of material for the filament 70, a defect opening, for example in the human heart, can be closed by this means and, if appropriate, tissue can even grow onto it there.

FIG. 11c shows an alternative to the complete closure, by the filament 70, of the support structure formed by the wire-like element 10, in which alternative the filament 70 is woven through only a partial area. Here, in particular, the through-opening 50 is closed so that, if appropriate, it is also possible to completely occlude a defect opening which is smaller compared to the dimensions of the implantable device. On the other hand, however, this embodiment variant can also be used only for partial occlusion of defect openings, since the woven filament is arranged only in the area 71.

In a further alternative embodiment, as is represented in FIG. 11d, a filament is no longer woven into the support structure, and instead a tissue or scrim is inserted therein as membrane 72. In the embodiment variant shown in FIG. 11d, however, this membrane 72 does not fill the entire surface of the distal portion and proximal portion of the device 1 and instead leaves an edge area 38 (in the case shown) in which no membrane is arranged. The latter, in the case shown, is integrated only into the proximal portion, but in an alternative embodiment it can also be integrated into the distal portion, in which case an edge area not covered by the membrane can then also be left in the proximal portion.

In a further alternative embodiment, as is shown in FIG. 11e, both the proximal and also the distal disk-shaped portions are provided with such a membrane 72. The two proximal and distal portions are arranged offset in relation to one another, that is to say the intermediate portion with the through-opening is not arranged centrally in the two proximal and distal portions, so that the two membranes also only partially overlap one another in the plan view. This is intended to show that it is possible to apply membranes in any desired manner on the support structure of the implantable devices.

FIGS. 12, 12a and 12b show further embodiments of a membrane 73 designed according to the invention. This has protruding arms 74 distributed about its circumference. Securing on the proximal and/or distal portion of an implantable device is made possible by the arms either being threaded through the meshes formed by the wire-like element 10 and/or through loops or hoops in the edge area of the distal and/or proximal end. After being pushed through, the arms are then preferably placed on one another and secured on the inner membrane surface 75, in particular by sewing, adhesive bonding, welding, crimping or another mode of securing. In principle, any other type of membrane can also be secured in the edge area of the proximal and/or distal portion by this manner of mechanical securing. The membrane or membrane-forming structure or membrane-like structure can be positioned in each area within the support structure of the implantable device 1, in particular in the proximal portion and/or distal portion and/or in the intermediate portion area.

FIG. 12a shows the membrane 73 according to FIG. 12 in a position that is secured on a support structure of an implantable device 1. Here, the support structure is placed onto the membrane, and the protruding arms 74 are laid around the edge 21 of the support structure of the implantable device and secured on the inner face which points toward the distal portion 30. In the case shown, the arms 74 are sewn, at their respective ends, through the support structure in the proximal portion 20 and onto the membrane surface 75 arranged on the proximal side of the support structure. In the embodiment shown according to FIG. 12a, the membrane 73 is thus secured only on the proximal portion. Securing can likewise also take place on the distal portion or on both. The membrane is preferably secured in such a way that straightforward release and locking of the implantable device is still ensured.

FIG. 12b shows a further embodiment of a support structure with inserted membrane 73. The support structure is annular and can be formed in particular from a cut tube, although likewise from a coiled wire-like element 10. The arms 74 are pushed through eyelets 13 and, as already in FIG. 12a, secured on the jacket surface 75, in particular by sewing, adhesive bonding, etc. The eyelets 13 can either be formed in a cut tube, which forms the support structure, or upon coiling by the wire-like element. As many eyelets as are needed are formed inside the support structure, in which case, for securing purposes, it is of course also possible in principle to use the loops at the edge of the support structure in order to push the arms 74 of the membrane through them and thus secure the membrane there.

A further variant, not shown in the figures, involves dipping the support structure in order to form a membrane-like structure. In this case, the support structure is dipped in particular into a film-forming material, after which a film, which is membrane-like, remains in the support structure. Depending on the choice of material for the dip medium, specific effects of the membrane can thus be achieved, in particular a hydrophobic or hydrophilic surface, especially to facilitate growth of tissue thereon. This choice of material can also be made so as to allow air and/or water permeability. Particularly suitable materials for the dip material are one or more monomers which form a natural or synthetic polymer, in particular by polyaddition, polymerization or polycondensation. Particularly suitable examples are polycarbonates, polyester, polyamides, polyolefins or polyurethane. Natural resins are also suitable provided that they are film-forming.

FIGS. 13a to 13g show the release of the implantable device 1 according to the present invention. Here, the implantable device is arranged in the defect opening 2 in the wall 3. For this purpose, a catheter 5, with an advancing tube 4 therein, is brought into the area of the defect opening 2. In the second step (FIG. 13b), the advancing tube 4 is guided through the opening 2. In the third step, the implantable device 1 is pushed out of the advancing tube 4, said device 1 being secured on a guide wire 6. The distal portion 30 of the implantable device first deploys. In the subsequent step (FIG. 13d), the advancing tube 4 is drawn back out from the opening 2, and the intermediate portion 40 deploys. The distal portion 30 now bears on the distal outer face 7 of the wall 3. Upon further withdrawal of advancing tube 4 and catheter 5, the implantable device 1 is pushed further on the guide wire out of the advancing tube 4, initially still in an elongate form. Retaining wires 80 which are secured on the proximal portion, and which can better be seen from FIGS. 14a to 14c, are still arranged on the guide wire and in the advancing tube. In the next and penultimate deployment step, shown in FIG. 13g, the implantable device is pushed completely out of the advancing tube. The retaining wires are still connected to the proximal portion 20. In the last step, which is shown in FIG. 13f, the guide wire and the retaining wires are likewise drawn back into the advancing tube. The implantable device has completely assumed its secondary shape in which the proximal portion 20 lies on the proximal outer face 8 and the distal portion 30 lies on the distal outer face 7 of the wall 3.

FIGS. 14a to 14c show the arrangement of retaining wires which, according to the invention, belong to the positioning system as shown in FIGS. 13a to 13g. It is possible for just one retaining wire to be threaded through all the loops or hoops at the proximal end and/or distal end, with formation of a loop for passage of the guide wire, or without formation of a loop. The embodiment with only one wire, which is threaded through all these hoops, is not shown in FIG. 14. However, FIG. 14a shows the embodiment variant in which two retaining wires 80, 81 are each drawn through half of the hoops or loops present, the guide wire 6 being threaded through a loop opening 82 formed by both retaining wires 80, 81. The two retaining wires are doubled in this area to form the loop. Both loops cover one another within a certain area and form between each other the loop opening 82. By guiding the guide wire through this loop opening 82 and pulling on both retaining wires, a fixed unit is obtained between the two retaining wires, the guide wire and the implantable device.

In an alternative embodiment, as shown in FIG. 14b, a chain is formed from retaining wires, this chain comprising loops 83 engaging in one another. In the embodiment shown in FIG. 14b, the guide wire is only threaded through the last loop 83 and thus also holds all the other ones secure, because these are linked to one another. In the variant shown in FIG. 14b, only four retaining wires are provided, whereas, in the variant shown in FIG. 14c, a retaining wire 80 is in each case threaded through each of the loops 22 at the proximal end of the device. These are all chained together, the guide wire again being pushed through the last loop 83. By pulling on the retaining wires a unit is once again formed between these, the guide wire 6 and the loops at the proximal end 24 of the implantable device, so that it is possible to direct the implantable device via the guide wire and along this. If all the hoops/loops at the proximal end (or also at the distal end) are brought together at one point (in the area of the through-opening), the provision of only one retaining wire and thus one loop and one guide wire suffices to create a firm connection for directing the implantable device. By contrast, if there is a noticeable through-opening between the loops or hoops at the proximal/distal end of the device 1, it is advantageous to use more than one retaining wire. For example, if 24 hoops or loops are provided at the proximal end of the device, it is also possible for 24 retaining wires to be provided. In principle, even more retaining wires can be provided if this appears advantageous.

If it transpires that the implantable device is to be removed again from the implantation site, in particular because the desired effect has in the meantime taken place, or because the implantable device was implanted at the wrong place, it is also possible, according to the invention, to remove it again and/or extract it with the positioning system as discussed above. For this purpose, a guide wire 9 and at least one extraction wire 90 are provided. However, the guide wire 9 can also be the guide wire 6 represented in the preceding figures. The extraction wire 90 can also be identical to a retaining wire 80. For the extraction of the implantable device, the extraction wire is pushed through the support structure of the device to the distal side, the extraction wire being formed into a loop. The guide wire 9 is likewise pushed through the support structure to the distal side of the implantable device 1 and threaded through the loop 91 of the extraction wire. Thereafter, the extraction wire 90 is first pulled, then the guide wire together with the extraction wire. In this way, the extraction wire remains firmly on the guide wire, and both of these together remain firmly on the support structure of the implantable device 1 and can draw the latter into a catheter.

To permit not only a positioning of the implantable device, but also its extraction, a set is preferably sold containing such a positioning system with retaining wires, guide wire, advancing tube and catheter and, if appropriate, different configurations of the implantable devices.

Instead of the provision of the wire-like element, the entire implantable device 1 can also be formed from a cut tube. This, or the wire-like element according to FIGS. 1 to 14c, can also be treated chemically and/or mechanically, in particular etched, electropolished, microground or otherwise treated. This can also be done at least in partial areas. Membrane-like structures can likewise be formed in this way. Irrespective of whether a wire-like element or a (laser) cut tube is used, these are preferably made of a biocompatible material, in particular a metal or a metal alloy, in particular high-grade steel, or a plastic, such as polycarbonate, in particular a shape-memory material, such as nitinol. The membranes, membrane-forming or membrane-like structures can likewise be made of a natural or synthetic material, in particular a gauze made of a polymer or of cotton or another natural material. Dacron filaments and carbon fibers are likewise suitable. Here too, account is preferably taken of the biocompatibility of the material. The implantable device according to the invention is of particular interest in the area of VSD and ASD, that is to say arterial septal defects and ventricular septal defects.

FIGS. 16 to 16c show various variants for connecting the two wire ends 11, 12 of the wire-like element 10 to one another in order to avoid injury to the tissue of the human or animal body surrounding the implantable device. As is shown in FIG. 16, the connection of these two ends 11, 12 is possible on the one hand by a sleeve 100. A force can be applied, for example at the location 101 indicated by the two arrows, in order to press the sleeve together there. This can be done, for example, with a hammer, forceps or similar aids. Adhesive bonding inside the sleeve is also possible, in which case, for example, after insertion of the two ends 11, 12 into the sleeve, the latter is filled with an adhesive. Welding or soldering of the ends of the sleeve is also possible, or any other desired form of closure of the latter.

Another variant of the joining together of the wire ends 11, 12 is shown in FIG. 16*a*. Here, the two ends are twisted together, so that a hold preventing undesired opening is afforded. Such mutual twisting of the wire ends is itself usually sufficient to prevent undesired loosening. In addition, however, at least one weld point or soldering point can, if appropriate, also be applied which connects the two wire ends still more firmly together.

Laser welding or adhesive bonding of the wire ends is also possible, as is shown in FIG. 16*b*. Here, several connection points 102 are applied by spot welding, adhesive bonding or the like between the two wire ends.

A further alternative solution to connecting the two wire ends is shown in FIG. 16*c*. Here, the ends 11, 12 of the wire-like element are connected to one another via a very fine spiral 103. The latter can also be designated as a microspiral. In addition, an adhesive connection is preferably provided between the spiral and the ends 11, 12 in order to effectively prevent undesired loosening of the connection. Of course, other variants of the connection of the ends of the wire-like element are also possible, in particular also combinations of the embodiments shown in FIGS. 16 to 16*c*. The aforementioned weaving in the support structure is in principle also possible. Here too, the wire ends can be additionally fixed in the support structure by adhesive bonding, welding, pressing, etc.

FIGS. 17*a* to 17*e* show the principle organization of the production of an implantable device according to the invention. First, as is indicated in FIG. 17*a*, a basic coil shape of the support structure is produced. It is preferably produced by hand by intertwining of a wire-like element or by cutting of a tubular element in such a way as to obtain a tissue, scrim, net or a corresponding support structure. In a second step, the basic coil shape of the support structure is annealed in an oven 110 in order to stabilize the basic coil shape. The material used for the support structure is a shape-memory material, in particular nitinol or, for example, also a plastic, such as polycarbonate. After the annealing step, the basic coil shape is formed into the desired secondary shape, as is indicated in FIG. 17*c*. This has, for example, one of the embodiments represented in the preceding figures or any desired other configuration suitable for the particular application of the implantable device. A further production step involves annealing of the secondary shape in the oven 110, as is indicated in FIG. 17*d*. Here, the secondary shape is imprinted on the material permanently such that, after elongation of the support structure or implantable device for introducing it through a catheter into a patient's body, and for subsequently pushing it out from the catheter, said support structure or implantable device automatically assumes its secondary shape. After the annealing and cooling, the shape of the implantable device shown in FIG. 17*e* is obtained for example. This implantable device can then be applied, for example, in the area of VSD and ASD.

FIGS. 18*a* to 18*j* show an alternative embodiment of the release of the implantable device 1 according to the present invention. Here, as has been described with reference to FIGS. 13*a* to 13*g*, the implantable device is fitted in the defect opening 2 in the wall 3, the catheter 5 with the advancing tube 4 being pushed through the defect opening 2, and the implantable device 1 being pushed out of the advancing tube 4. The distal portion 30 deploys. The advancing tube 4 is drawn back out of the opening 2, and the intermediate portion 40 deploys. In doing so, the distal portion 30 bears on the distal outer face 7 of the wall 3. In the next release step, which is shown in FIG. 18*c*, the implantable device is pushed completely out of the advancing tube and the latter has already been drawn back out of the opening 2.

Figure 20:
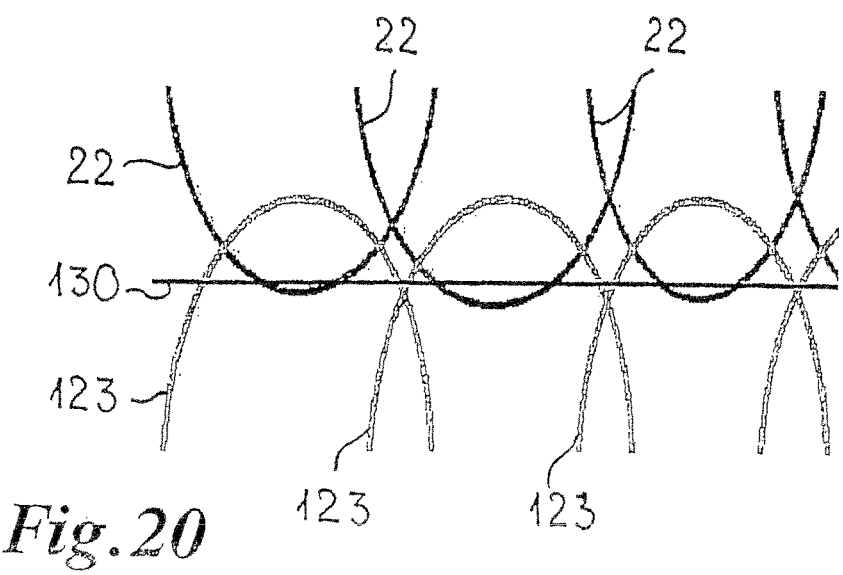

On the proximal side, with respect to the wall 3, the implantable device is pushed still further out of the advancing tube, together with an auxiliary structure 120, and, in this embodiment, three retaining wires 130, 131, 132. The retaining wires connect the proximal end 24 of the proximal portion 20 and the distal end 121 of the distal portion 122 of the auxiliary structure 120 to one another (better seen in FIGS. 19*a* and 19*b*). Instead of three retaining wires, it is also possible, for example, to provide only one or two, or also more than three. The connection can be done, for example, as is shown in FIG. 20. There, the terminal loops 22, 123 or hoops of the support structure of the implantable device and the auxiliary structure are placed opposite one another and partially overlapping one another, and the retaining wire 130 is threaded alternately over and under the filaments or wires of the loops. The retaining wires are guided along the auxiliary structure in the advancing tube. They can also be guided outside of the latter. In the view according to FIG. 18*e*, the proximal portion 20 and the auxiliary structure are pushed further out of the advancing tube and deployed. In the view according to FIG. 18*f*, the proximal portion 20 is already almost completely deployed, likewise the distal portion 122 of the auxiliary structure 120. The retaining wires are still guided along the auxiliary structure. When the retaining wires are drawn back and the implantable device and auxiliary structure are further deployed, the retaining wires in the view according to FIG. 18*g* extend radially outward (FIG. 19*a*). Upon further drawing back of the retaining wires, these are pulled out of the loops 22, 123 or hoops of the structures and extend radially outward from the facing edges of the structures (FIG. 18*h*). When the retaining wires are drawn further back into the advancing tube, the distal end 121 of the auxiliary structure and the proximal end 24 of the proximal portion of the support structure of the implantable device separate from one another, as is indicated in FIGS. 18*i* and 19*b*. After the further drawing-back of the retaining wires and separation of the structures from one another, the support structure of the implantable device is released and deployed completely in the opening 2. The proximal portion 20 bears on the proximal outer face 8 of the wall 3 (FIG. 18*j*). The distal portion 122 of the auxiliary structure 120 is likewise completely deployed. The auxiliary structure can subsequently be drawn back into the advancing tube and thus removed from the implantation site. With this method of releasing an implantable device, a proximal portion which may be difficult to deploy can advantageously be completely deployed. It is no longer even necessary for the end diameters of the deployed proximal end of the support structure of the implantable device and of the distal end 121 of the auxiliary structure to match. The diameter of the distal end 121 can even be greater, provided, however, that the proximal portion 20 of the implantable device can be deployed without any problem.

In addition to the embodiments described above and shown in the figures, others may also be envisioned in which only a wire-like element is used to form the support structure. It is thus possible to form proximal and/or distal portions that protrude in particular in a dish shape, although numerous other shapes are also possible.

LIST OF REFERENCE NUMBERS

1 implantable device
2 defect opening 3 wall
4 advancing tube
5 catheter
6 guide wire
7 distal outer face
8 proximal outer face
9 guide wire
10 wire-like element
11 end
12 end
13 eyelet
20 proximal portion
21 edge area
22 loop
23 edge area
24 proximal end
25 surface
26 e-shaped hoop
27 inner space
28 edge area
29 partial area
30 distal portion
31 edge area
32 loop
33 edge area
34 distal end
35 surface
36 edge area
37 opening
38 edge area
40 intermediate portion
41 cover area
42 attachment area
50 through-opening
51 through-opening
52 opening
60 arrow
61 arrow
62 area
63 longitudinal axis
70 filament
71 area with filament
72 membrane
73 membrane
74 arms
75 inner membrane surface
80 first retaining wire
81 second retaining wire
82 loop opening
83 loop
90 extraction wire
91 loop
100 sleeve
101 arrows/pinch point
102 connection points
103 spiral
110 oven
120 auxiliary structure
121 distal end
122 distal portion
123 loop
130 retaining wire
131 retaining wire
132 retaining wire

What is claimed is:

1. An implantable device to be used in a human and/or animal body to at least partially occlude a defect opening in a wall in said body, comprising:
a support structure transformable from a primary shape of an elongate tube having an elongate tubular opening extending between two open tubular ends and a first length-to-width ratio along a longitudinal axis in a first operating state into a secondary shape having a second length-to-width ratio along said longitudinal axis in a second operating state wherein said first length-to-width ratio is greater than said second length-to-width ratio,
wherein said support structure comprises a single wire-like element of said elongate tube having said tubular opening extending between said two open tubular ends, said wire-like element having a mesh structure having a plurality of loops forming a net,
wherein, in said secondary shape of said support structure, said support structure has a proximal portion, an intermediate portion, a distal portion, a proximal outer edge and a distal outer edge, wherein said proximal portion, said distal portion and said intermediate portion of said support structure are formed by said mesh structure and wherein said proximal portion and said distal portion are offset from said intermediate portion, and said proximal portion and said distal portion are configured to engage opposing sides of said wall and a portion of said intermediate portion is configured to engage said defect opening and at least partially occludes said defect opening,
wherein, in said secondary shape of said support structure, said proximal portion and said distal portion are of a proximal disk configuration formed by said mesh structure and a distal disk configuration formed by said mesh structure, respectively, with said proximal disk configuration and said distal disk configuration each having a shape of a plate, and with said intermediate portion arranged between said proximal portion and said distal portion, said intermediate portion having a reduced diameter compared to said proximal and/or said distal portion,
wherein said distal outer edge of said support structure of said secondary shape is defined by a distal end of said two open tubular ends of said support structure of said primary shape,
wherein said distal outer edge of said distal disk configuration of said support structure of said secondary shape has a greater diameter than a diameter of said distal end of said elongate tube of said support structure of said primary shape, and
wherein the mesh structure in each of the proximal portion and the distal portion extends radially around the elongate tubular opening in the secondary shape of the support structure.

2. The implantable device as claimed in claim 1, wherein said proximal portion includes said outer edge portion and said plurality of loops defining said outer edge portion of said proximal portion are directed radially outwardly in said secondary shape.

3. The implantable device as claimed in claim 1, wherein at least one of said proximal disk configuration and said distal disk configuration in said secondary shape is substantially flat.

4. The implantable device as claimed in claim 1, wherein said distal portion includes said distal outer edge and said plurality of loops define said distal outer edge.

5. The implantable device as claimed in claim 4, wherein said plurality of loops defining said distal outer edge are interlocked and/or interlaced.

6. The implantable device as claimed in claim 1, wherein, in said secondary shape of said support structure, the elongate tubular opening in said support structure is configured for partial occlusion of said defect opening.

7. The implantable device as claimed in claim 1, wherein at least a portion of said support structure in said primary shape and/or said secondary shape is asymmetrically and/or irregularly configured.

8. The implantable device as claimed in claim 7, wherein said single wire-like element of said support structure has a thickness and a concentration of material and said thickness and said concentration of material are different across said support structure from said proximal portion to said distal portion.

9. The implantable device as claimed in claim 8, wherein said support structure includes partial areas which are formed from said single wire-like element, said single wire-like element having different diameters along a longitudinal length of said support structure.

10. The implantable device as claimed in claim 8, wherein said concentration of material of said single wire-like element in an edge area provides for partial stiffening.

11. The implantable device as claimed in claim 1, wherein said support structure in said primary shape is configured as a stent.

12. The implantable device as claimed in claim 1, wherein one or more membranes or membrane-like or membrane-forming structures are incorporated into said support structure or applied to said support structure.

13. The implantable device as claimed in claim 12, wherein said one or more membrane-forming structures are formed by interweaving of at least one filament.

14. The implantable device as claimed in claim 12, wherein said one or more membrane-forming structures have a cross section differing from that of said single wire-like element, or comprises a braid, a scrim or a weave.

15. The implantable device as claimed in claim 12, wherein said one or more membrane-like structures are formed by dipping said support structure into a film-forming material.

16. The implantable device as claimed in claim 12, wherein said one or more membrane-like structures are formed from a weave, a scrim or other textile.

17. The implantable device as claimed in claim 12, wherein said one or more membranes, or membrane-like or membrane-forming structures are arranged proximally, distally or substantially centrally in said support structure.

18. The implantable device as claimed in claim 1, wherein said single wire-like element of said support structure is chemically and/or mechanically treated in at least a partial area.

19. The implantable device as claimed in claim 1, wherein said single wire-like element of said support structure is made of a metal or a metal alloy, a high-grade steel, a plastic, or a shape-memory material.

20. The implantable device as claimed in claim 1, wherein said distal outer edge of said distal disk configuration is further radially away from said longitudinal axis than any other portion of said distal disk configuration.

21. The implantable device as claimed in claim 1, wherein said proximal outer edge is defined by a proximal end of said two open tubular ends, and
wherein said proximal outer edge of said proximal disk configuration of said support structure in said secondary shape has a greater diameter than a diameter of said proximal end of said elongate tube of said support structure in said primary shape.

22. The implantable device as claimed in claim 21, wherein said proximal outer edge of said proximal disk configuration is further radially away from said longitudinal axis than any other portion of said proximal disk configuration.

* * * * *